US012599683B2

(12) United States Patent
Thierry et al.

(10) Patent No.: US 12,599,683 B2
(45) Date of Patent: Apr. 14, 2026

(54) MAPPING NANOPARTICLES

(71) Applicants: Ferronova Pty Ltd, Adelaide (AU); Purdue Research Foundation, West Lafayette, IN (US)

(72) Inventors: Benjamin Thierry, Fitzroy (AU); Melanie Ruth Maria Nelson, Brompton (AU); Valentina Milanova, Mawson Lakes (AU); Nicole Dmochowska, Glandore (AU); Thi Hanh Nguyen Pham, Yagoona (AU); Brian Stanley Hawkett, Mona Vale (AU); Ramesh Mukkamala, West Lafayette, IN (US); Philip Stewart Low, West Lafayette, IN (US)

(73) Assignees: Ferronova Pty LTD, Adelaide (AU); Purdue Research Foundation

( * ) Notice: Subject to any disclaimer, the term of this patent is extended or adjusted under 35 U.S.C. 154(b) by 0 days.

(21) Appl. No.: 18/289,215

(22) PCT Filed: May 12, 2022

(86) PCT No.: PCT/AU2022/050450
§ 371 (c)(1),
(2) Date: Nov. 1, 2023

(87) PCT Pub. No.: WO2022/241506
PCT Pub. Date: Nov. 24, 2022

(65) Prior Publication Data

US 2024/0415986 A1 Dec. 19, 2024

(30) Foreign Application Priority Data

May 19, 2021 (AU) ................................ 2021901499

(51) Int. Cl.
*A61K 49/00* (2006.01)
*A61K 49/18* (2006.01)
*A61P 35/00* (2006.01)

(52) U.S. Cl.
CPC ...... *A61K 49/0093* (2013.01); *A61K 49/0032* (2013.01); *A61K 49/0034* (2013.01); *A61K 49/0054* (2013.01); *A61K 49/1854* (2013.01); *A61P 35/00* (2018.01)

(58) Field of Classification Search
CPC ........................ A61K 49/0054; A61K 49/1854
See application file for complete search history.

(56) References Cited

U.S. PATENT DOCUMENTS 11,786,613 B2 * 10/2023 Bartlett .............. A61K 49/1857 424/9.323
2011/0129417 A1 * 6/2011 Hawkett ............ A61K 41/0052 424/1.61
2015/0125401 A1 5/2015 Gendelman et al.
2020/0330624 A1 10/2020 Yang et al.

FOREIGN PATENT DOCUMENTS

EP 3037107 6/2016
WO WO-2018111989 A1 * 6/2018 ............. A61P 35/04
WO 2021016392 1/2021
WO 2021097537 5/2021

OTHER PUBLICATIONS

International Search Report and Written Opinion in corresponding International Patent Application No. PCT/AU2022/050450, dated Jul. 8, 2022.

International Journal of Nanomedicine article "A synthetic urinary probe-coated nanoparticles sensitive to fibroblast activation protein a for solid tumor diagnosis". V. 12; 2017; Xinwei Feng et al.

* cited by examiner

*Primary Examiner* — Robert S Cabral
(74) *Attorney, Agent, or Firm* — Faegre Drinker Biddle & Reath LLP

(57) ABSTRACT

Nanoparticulate material suitable for administration to a subject, the nanoparticulate material having bound to its surface: (a) copolymeric steric stabiliser that promotes dispersion of the nanoparticulate material in a liquid, wherein the copolymeric steric stabiliser comprises (i) an anchoring polymer segment having one or more binding groups that bind the copolymeric steric stabiliser to the nanoparticulate material, and (ii) a steric stabilising polymer segment that is different from the anchoring polymer segment, and (b) copolymeric mapping moiety comprising (i) an anchoring polymer segment having one or more binding groups that bind the copolymeric mapping moiety to the nanoparticulate material, (ii) one or more mapping groups comprising an agent that specifically binds to fibroblast activation protein (FAP), and (iii) a coupling polymer segment that is different to the anchoring polymer segment, wherein the coupling polymer segment couples the anchoring polymer segment to the one or more mapping groups.

13 Claims, 10 Drawing Sheets

MAPPING NANOPARTICLES

CROSS-REFERENCE TO RELATED APPLICATIONS

The present application is a U.S. National Phase of International Application No. PCT/AU2022/050450, filed on May 12, 2022 and entitled MAPPING NANOPARTICLES which claims the benefit of Australian Application Serial No. 2021901499, filed May 19, 2021 and entitled MAPPING NANOPARTICLES, the entire disclosures of which are hereby expressly incorporated herein by reference.

TECHNICAL FIELD

The present application relates in general to nanoparticles, compositions comprising the same and their use in mapping, diagnostic and therapeutic applications.

BACKGROUND

Surgical tumour resection is a standard of care for many cancers, especially when the disease is localised to a single solid tumour. However, surgery is invasive and failure to pinpoint residual neoplastic tissue can result in positive surgical margins, which correlate with regional recurrence and poor patient outcomes. Further, the accurate identification of tumour margins is critical to the efficacy of non-surgical treatment modalities, such as external beam radiotherapy, brachytherapy and focal therapy, each of which require the best possible characterisation of the location and extent (e.g., volume) of the tumour.

For example, radical prostatectomy is the standard treatment for aggressive and intermediate prostate cancer. However, following this surgical intervention around 20% of patients' exhibit urinary incontinence and around 70% of patients will exhibit erectile dysfunction. Due to these serious side effects, men with limited life expectancy and slow-growing, low-risk disease are often recommended to "watch and wait" before undergoing surgery. Alternatively, some patients are offered therapies prior to radical prostatectomy, such as external beam radiotherapy, brachytherapy, and focal therapy. Although such therapies are associated with reduced side effects, they are not as effective as partial or complete surgical tumour resection. A contributing factor to the reduced efficacy of these alternative treatment modalities is the limitations of existing medical imaging, which do not provide adequate spatial resolution to identify the boundaries and margins of the primary tumour. For example, prostate specific membrane antigen positron emission tomography/computed tomograph (PET-PSMA) can underestimate tumour volume by 9-15% and multi-parametric magnetic resonance imaging (mpMRI) can underestimate the tumour volume by 11-20%. Due to the imaging deficiencies, focal therapy guidelines require that the margin of an ablation area surrounding the identified lesion be extended by up to 10 mm. However, even when the ablation area is extended, margin recurrence rates of 20-40% have been reported. Similar issues occur in other cancers where preservation of the organ and limiting normal tissue toxicity is critical, for example including but not limited to glioblastoma and pancreatic cancer.

Accordingly, there remains a need to develop new materials and compositions that accurately identify the margins of solid tumours to improve surgical resection by providing improved preoperative and/or intraoperative guidance, or so that less invasive treatment modalities, such focal therapy including cryoablation, focal laser ablation and high-frequency ultrasound ablation, photodynamic therapy, high-dose-rate and low-dose-rate brachytherapy, particle radiotherapy such as proton and carbon ion therapies, and external beam radiation therapy including intensity-modulated radiation therapy (IMRT), image-guided radiotherapy (IGRT), hypo-fractionated and ultra-high dose rates radiotherapy can more accurately target the full volume of the tumour and reduce exposure of non-target tissue.

SUMMARY

It has surprisingly been found nanoparticulate material according to the present invention selectively accumulates in the tumour microenvironment, thereby mapping the margin of solid tumours. Without wishing to be limited by theory, the combined function of the copolymeric steric stabiliser and the copolymeric mapping moiety at least in part enables the nanoparticulate material described herein to selectively bind to fibroblast activation protein (FAP) expressed by cells within the tumour microenvironment, for example, tumour-associated stromal cells.

Accordingly, in an aspect described herein, there is provided nanoparticulate material suitable for administration to a subject, the nanoparticulate material having bound to its surface: (a) copolymeric steric stabiliser that promotes dispersion of the nanoparticulate material in a liquid, wherein the copolymeric steric stabiliser comprises (i) an anchoring polymer segment having one or more binding groups that bind the copolymeric steric stabiliser to the nanoparticulate material, and (ii) a steric stabilising polymer segment that is different from the anchoring polymer segment, and (b) copolymeric mapping moiety comprising (i) an anchoring polymer segment having one or more binding groups that bind the copolymeric mapping moiety to the nanoparticulate material, (ii) one or more mapping groups comprising an agent that specifically binds to fibroblast activation protein (FAP), and (iii) a coupling polymer segment that is different to the anchoring polymer segment, wherein the coupling polymer segment couples the anchoring polymer segment to the one or more mapping groups.

The nanoparticulate material according to the invention advantageously exhibits improved blood half-life circulation to support systemic injections and/or does not substantially degrade in-vivo.

Without wishing to be limited by theory, it is believed the nanoparticulate material exhibits such advantageous properties at least through the copolymeric components bound to its surface. Those copolymeric components include the copolymeric steric stabiliser in combination with the copolymeric mapping moiety. Both the copolymeric steric stabiliser and the copolymeric mapping moiety comprise an anchoring polymer segment that bind the respective entities to the nanoparticulate material. The anchoring polymer segments have advantageously been found to be highly effective at maintaining both the copolymeric steric stabiliser and the copolymeric mapping moiety secured to the nanoparticulate material when, for example, located in an in vivo liquid environment. That in turn facilitates maintaining the nanoparticulate material in a dispersed form within that in vivo liquid environment. Those skilled in the art will appreciate aggregation of nanoparticulate material in an in vivo liquid environment can be detrimental in diagnostic and therapeutic applications.

Working in synergy with the imparted effect of improved dispersion within, for example, an in vivo liquid environment, again without wishing to be limited by theory, it is believed the copolymeric mapping moiety enables enhanced accumulation of the particulate material in the tumour microenvironment. Depending on the intended application, the nanoparticulate material, which also inherently accumulates in the tumour microenvironment by it being bound to the copolymeric mapping moiety, can advantageously be selected to perform a given task. For example, the nanoparticulate material may be provided in the form of magnetic nanoparticulate material for use in applications such as magnetic particle imaging (MPI) and magnetic resonance imaging (MRI) including low field MRI, MRI guided external beam radiotherapy, MRI guided focal ablation, MRI/Ultrasound fusion focal ablation, MRI guided biopsy, MRI/Ultrasound fusion guided biopsy, MRI guided surgery, MRI guided brachytherapy, MRI guided infrared camera guided biopsy or therapy, and photoacoustic guided biopsy or therapy.

The nanoparticulate material in accordance with the invention have therefore been found to be particularly effective at mapping tumour margin(s) in the subject and enhancing conventional methods for determining the location and extent (e.g., volume) of tumour lesions and therapeutic applications.

Those skilled in the art will appreciate the application of targeted nanoparticulate material in vivo can be adversely affected by undesirable protein adsorption that gives rise to a so called protein corona and can lead to a loss in binding efficiency at a target site. Not only can such protein adsorption reduce binding efficiency, it can also consequently reduce accumulation of the nanoparticulate material at a target site. Surprisingly, it has been found the combined use of the copolymeric steric stabiliser and the copolymeric mapping can also advantageously reduce the effect of adverse protein adsorption thereby improving the accumulation efficiency of the nanoparticulate material in the tumour microenvironment.

In one embodiment, the nanoparticulate material has bound to its surface: (c) copolymeric luminescent moiety comprising (i) an anchoring polymer segment having one or more binding groups that bind the polymeric luminescent moiety to the nanoparticulate material, (ii) one or more luminescent groups for emitting light or an acoustic signal in response to light that enables in vivo location visualisation of the nanoparticulate material, and (iii) a coupling polymer segment that is different to the anchoring polymer segment, wherein the coupling polymer segment couples the anchoring polymer segment to the one or more luminescent groups.

In one embodiment, the steric stabilising polymer segment comprises a polyacrylamide-co-polyalkylene oxide block copolymer.

In another embodiment, the coupling polymer segment consists of polyacrylamide.

In a further embodiment, the steric stabilising polymer segment comprises a polyacrylamide-co-polyalkylene oxide block copolymer, and the coupling polymer segment consists of polyacrylamide.

In one embodiment, the steric stabilising polymer segment has from 10 to 70 polymerised monomer residue units.

In another embodiment, the coupling polymer segment has from 15 to 100 polymerised monomer residue units.

In a further embodiment, the steric stabilising polymer segment has from 10 to 70 polymerised monomer residue units and the coupling polymer segment has from 15 to 100 polymerised monomer residue units.

In one embodiment, the nanoparticulate material is magnetic nanoparticulate material.

As described elsewhere herein, the nanoparticulate material selectively binds to fibroblast activation protein (FAP) expressed by cells within the tumour microenvironment.

In an embodiment, the cells within the tumour microenvironment are tumour-associated stromal cells.

In a further embodiment, the tumour-associated stromal cell is selected from a fibroblast, pericyte, an adipocyte, a mesenchymal stromal cell (MSC), an endothelial cell, and combinations thereof. In another embodiment, the tumour-associated stromal cell is selected from a pericyte, an endothelial cell, and combinations thereof.

In an embodiment, the agent that specifically binds to FAP is selected from a small molecule inhibitor and an antibody, or antigen-binding fragment thereof. In another embodiment, the small molecule inhibitor is a FAP inhibitor.

In a further embodiment, the one or more luminescent groups are selected from chemiluminescent, electroluminescent, photoluminescent, radioluminescent and thermoluminescent groups.

In another aspect disclosed herein, there is provided a composition suitable for administration to a subject, the composition comprising the nanoparticulate material according to the invention.

In an embodiment, the composition comprises a pharmacologically acceptable liquid carrier.

In another aspect disclosed herein, there is provided a use of the nanoparticulate material or the composition according to the invention in performing a therapeutic or diagnostic application on a subject.

Examples of suitable therapeutic or diagnostic applications include magnetic particle imaging (MPI), magnetic resonance imaging (MRI), MRI guided external beam radiotherapy, MRI guided focal ablation, MRI/Ultrasound fusion focal ablation, MRI guided biopsy, MRI/Ultrasound fusion guided biopsy, MRI guided surgery, MRI guided brachytherapy, MRI guided infrared camera guided biopsy or therapy, and photoacoustic guided biopsy or therapy.

The nanoparticulate material or composition according to the invention can be used in conjunction with in vivo imaging techniques including, but not limited to, ultrasound, MRI/ultrasound, X-ray, optical imaging, Computed Tomography (CT), Single Photon Emission Computed Tomography (SPECT), Positron Emission Tomography (PET), Fluorescence Resonance Energy Transfer (FRET), and Magnetic Resonance Imaging (MRI).

In another aspect disclosed herein, there is provided a use of the nanoparticulate material or composition according to the invention for in vivo imaging.

In another aspect disclosed herein, there is provided nanoparticulate material or composition according to the invention for use in in vivo imaging.

In another aspect disclosed herein, there is provided a use of the nanoparticulate material or composition according to the invention for the detection of cancer.

In another aspect disclosed herein, there is provided nanoparticulate material or composition according to the invention for use in the detection of cancer.

In an embodiment, the cancer is selected from prostate cancer, glioblastoma multiform, glioma, pancreatic cancer, colorectal cancer, breast cancer, head and neck cancer, gastric cancer, oesophageal cancer, ovarian cancer, sarcoma and lung cancer. In another embodiment, the cancer is a prostate cancer.

In another aspect disclosed herein, there is provided a use of the nanoparticulate material or composition according to the invention for mapping the tumour microenvironment In another aspect disclosed herein, there is provided nanoparticulate material or composition according to the invention for use in mapping the tumour microenvironment.

In an aspect disclosed herein there is provided a method for mapping a tumour margin in a subject, the method comprising:

a. administering the nanoparticulate material or composition according to the invention to the subject; and b. detecting the nanoparticulate material, wherein the nanoparticulate material accumulates in the tumour microenvironment, thereby mapping the tumour margin.

In an embodiment, the tumour margin is mapped in situ. The tumour may be mapped in situ before or after tumour tissue resection.

In an embodiment, the method further comprises determining clinical target volume (CTV) and/or gross target volume (GTV) prior to the administration of a treatment.

In an aspect disclosed herein there is provided a method for the treatment of cancer in a subject in need thereof, the method comprising:

a. administering the nanoparticulate material or composition according to the invention to the subject;

b. detecting a site where the nanoparticulate material accumulates;

c. administering an effective amount of a treatment for said cancer at the site of nanoparticulate material detection in step (b).

In an embodiment, the treatment is selected from surgery, radiotherapy, brachytherapy, photodynamic therapy, photothermal therapy, focal ablation therapy including cryoablation, focal laser ablation and high-frequency ultrasound ablation, chemotherapy, immunotherapy and combinations thereof.

In an embodiment, the nanoparticulate material is detected using an imaging technique selected from magnetic resonance imaging (MRI), ultrasound, X-ray, optical imaging, fluorescence imaging, Computed Tomography (CT), Single Photon Emission Computed Tomography (SPECT), Positron Emission Tomography (PET) and Fluorescence Resonance Energy Transfer (FRET).

In an embodiment, the method further comprises determining clinical target volume (CTV) and/or gross target volume (GTV) prior to the administration of a treatment in accordance with step (c).

In an aspect disclosed herein, there is provided a method for diagnosing cancer, the method comprising:

a. administering the nanoparticulate material or composition according to the invention to a subject; and b. detecting the nanoparticulate material;

wherein the detection of accumulated nanoparticulate material in tissue (such as vascular tissue) of the subject indicates that the subject has cancer.

Further aspects and embodiment of the invention are outlined and discussed in more detail below.

BRIEF DESCRIPTION OF THE FIGURES

Embodiments of the present disclosure will be discussed with reference to the accompanying non-limiting figures wherein.

DETAILED DESCRIPTION

Figure 1:
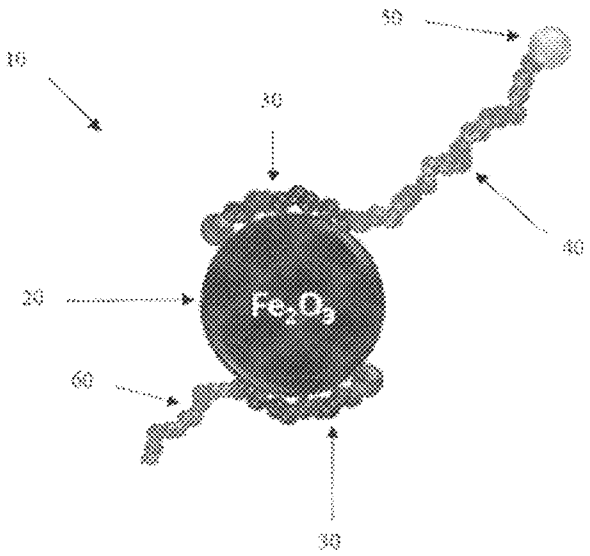
FIG. 1 is a schematic drawing illustrating nanoparticulate material in accordance with the invention.

In this specification a number of terms are used which are well known to a skilled addressee. Nevertheless for the purposes of clarity a number of terms will be defined.

By the term "subject" is meant either an animal or human subject. By "animal" is meant primates, livestock animals (including cows, horses, sheep, pigs and goats), companion animals (including dogs, cats, rabbits and guinea pigs), and captive wild animals (including those commonly found in a zoo environment). Laboratory animals such as rabbits, mice, rats, guinea pigs and hamsters are also contemplated as they may provide a convenient test system. In some embodiments, the subject is a human subject.

By the nanoparticulate material or composition according to the invention being "suitable" for administration to a subject is meant that administration of the composition to a subject will not result in unacceptable toxicity, including allergenic responses and disease states.

By "administration" of the nanoparticulate material or composition to a subject is meant that the nanoparticulate material or composition is presented such that the nanoparticulate material can be transferred to the subject. There is no particular limitation on the mode of administration, but this will generally be by way of oral, parenteral (including subcutaneous, intradermal, intramuscular, intravenous, intracerebrally, intranasally, intrathecal, and intraspinal), inhalation (including nebulisation), topical, rectal and vaginal modes. The nanoparticulate material or composition may also be administered directly into a tumour and/or into tissue adjacent one or more segments of a tumour or administered directly into blood vessels.

By "pharmacologically acceptable" is meant being suitable for administration to a subject. In other words, administration of the relevant material to a subject should not result in unacceptable toxicity, including allergenic responses and disease states.

As a guide only, a person skilled in the art may consider "pharmacologically acceptable" as an entity approved by a regulatory agency of a federal or state government or listed in the US Pharmacopeia or other generally recognised pharmacopeia for use in animals, and more particularly humans.

Having said that, those skilled in the art will appreciate the suitability of the nanoparticulate material or composition according to the invention for administration to a subject and whether or not it or its constituent components would be considered pharmacologically acceptable, will to some extent depend upon the mode of administration selected. Thus, the mode of administration may need to be considered when evaluating whether or not a composition or constituent component thereof is suitable for administration to a subject or if it is pharmacologically acceptable.

By the nanoparticulate material being "dispersed throughout" a liquid carrier is meant that the nanoparticulate material presents as a dispersed phase throughout the liquid carrier which itself, relative to the particulate material, presents as a continuous liquid medium or phase. In other words, a composition according to the invention might be described as comprising a suspension or dispersion of the nanoparticulate material throughout a liquid carrier.

As used herein, the term "liquid" in the context of the liquid carrier is intended to mean a vehicle in which the nanoparticulate material is dispersed throughout and which is in a liquid state at least at the temperature of intended use of compositions in accordance with the invention. Typically, a liquid carrier will be considered to be in a "liquid" state if, in the absence of a stabiliser, particulate material dispersed throughout the carrier can flocculate or settle out from the carrier to form a sediment. In other words, if the particulate material can move relatively freely in the vehicle, then it is considered "liquid".

A liquid carrier used in accordance with the invention may be made up of one or more different liquids. Suitable pharmacologically acceptable liquid carriers are described in Martin, Remington's Pharmaceutical Sciences, $18^{th}$ Ed., Mack Publishing Co., Easton, PA, (1990), and include, but are not limited to, liquids that may be sterilised such as water and oils, including those of petroleum, animal, vegetable, mineral or synthetic origin, such as peanut oil, soya bean oil, mineral oil, sesame oil, and the like. Other liquid carriers include methylene glycol, propylene glycol, polyethylene glycol, polypropylene glycol, ethanol, isopropyl alcohol, benzyl alcohol. Water or soluble saline solutions and aqueous dextrose and glycerol solutions are preferably employed as liquid carriers, particularly for injectable solutions.

Compositions in accordance with the invention may comprise one or more pharmacologically acceptable additives known to those in the art. For example, the liquid carrier may comprise one or more additives such as wetting agents, de-foaming agents, surfactants, buffers, electrolytes, preservatives, colourings, flavourings, and sweeteners.

The particular nature of a liquid carrier and any additive (if present) will in part depend upon the intended application of the composition. Those skilled in the art will be able to select a suitable liquid carrier and additive (if present) for the intended application of the composition.

The nanoparticulate material may be administered in, as appropriate, a treatment or diagnostic effective amount. A treatment or diagnostic effective amount is intended to include an amount which, when administered according to the desired dosing regimen, achieves a desired therapeutic or diagnostic effect, including one or more of: alleviating the symptoms of, preventing or delaying the onset of, inhibiting or slowing the progression of, diagnosing, or halting or reversing altogether the onset or progression of a particular condition being treated and/or assessed.

Suitable dosage amounts and dosing regimens to achieve this can be determined by the attending physician and may depend on the particular condition being treated or diagnosed, the severity of the condition as well the general age, health and weight of the subject.

Dosing may occur at intervals of minutes, hours, days, weeks, months or years or continuously over any one of these periods. Suitable dosages of the particulate material per se may lie within the range of about 0.1 ng per kg of body weight to 1 g per kg of body weight per dosage. The dosage may be in the range of 1 μg to 1 g per kg of body weight per dosage, such as is in the range of 1 mg to 1 g per kg of body weight per dosage. In one embodiment, the dosage may be in the range of 1 mg to 500 mg per kg of body weight per dosage. In another embodiment, the dosage may be in the range of 1 mg to 250 mg per kg of body weight per dosage. In yet another embodiment, the dosage may be in the range of 1 mg to 100 mg per kg of body weight per dosage, such as up to 50 mg per kg of body weight per dosage.

Nanoparticulate material or compositions in accordance with the invention may be administered in a single dose or a series of doses.

Where the nanoparticulate material or compositions in accordance with the invention are suitable for parenteral administration, they will generally be in the form of an aqueous or non-aqueous isotonic sterile injection solution that may contain one or more of an anti-oxidant, buffer, bactericide or solute which renders the composition isotonic with the blood of the intended subject. Such compositions may be presented in unit-dose or multi-dose sealed containers, for example, ampoules and vials.

Upon administration, nanoparticulate material or compositions in accordance with the invention may be diluted in vivo. For example, dilution can occur when they are administered orally or parenterally. In that case, the liquid carrier of the composition may become so dilute in vivo that the surrounding liquid environment throughout which the particulate material is dispersed becomes more representative of an in vivo liquid (i.e. a biological liquid/fluid within the subject) than the original liquid carrier. For example, once administered parenterally, the nanoparticulate material might more aptly be described as being dispersed throughout blood rather than an original liquid carrier of the composition. Under those circumstances, it may be convenient to refer to the nanoparticulate material as being dispersed throughout an in vivo liquid carrier (i.e. a biological liquid/fluid within the subject). With the exception of any compositional differences between a liquid carrier of compositions in accordance with the invention and an in vivo liquid carrier, matters described herein relating to the liquid carrier of the composition will also generally apply to an in vivo liquid carrier.

As used herein, the expression "tumour microenvironment" refers to a heterogeneous population of non-cancerous cells surrounding and/or infiltrating a tumour, which are essential to the functionality, physiology and metastasis of the tumour. The skilled person will appreciate that the tumour microenvironment comprises a range of different cell types that may differ based on the size, location, type and stage of a tumour, illustrative examples of which include fibroblasts, pericytes, adipocytes, mesenchymal stromal cells (MSCs), cancer cells and endothelial cells. While the cells of the tumour microenvironment are non-cancerous, tumours recruit and or regulate such cells to provide a favourable environment to facilitate cancer growth. Accordingly, cells comprised within the tumour microenvironment may be referred to as "cancer-associated" or "tumour-associated".

In an embodiment, the nanoparticulate material disclosed herein selectively binds to fibroblast activation protein (FAP) expressed by cells within the tumour microenvironment.

In an embodiment, the cells within the tumour microenvironment are tumour-associated stromal cells.

In an embodiment, the tumour-associated stromal cell is selected from a fibroblast, pericyte, an adipocyte, a mesenchymal stromal cell (MSC), a cancer cell, an endothelial cell, and combinations thereof. In another embodiment, the tumour-associated stromal cell is selected from a pericyte, an endothelial cell, and combinations thereof.

The term "about" or "approximately" means within an acceptable range for the particular value as determined by one of ordinary skill in the art, which will depend in part on how the value is measured or determined, e.g. the limitations of the measurement system. For example, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5 fold, and more preferably within 2 fold, of a value. Unless otherwise stated, the term 'about' means within an acceptable error range for the particular value, such as ±1-20%, preferably ±1-10% and more preferably ±1-5%.

Where a range of values is provided, it is understood that each intervening value, between the upper and lower limit of that range and any other stated or intervening value in that stated range, is encompassed within the disclosure. The upper and lower limits of these smaller ranges may independently be included in the smaller ranges, and are also encompassed within the disclosure, subject to any specifically excluded limit in the stated range. Where the stated range includes one or both of the limits, ranges excluding either both of those included limits are also included in the disclosure.

A phrase referring to "at least one of" a list of items refers to any combination of those items, including single members. As an example, "at least one of: a, b, or c" is intended to cover: a, b, c, a-b, a-c, b-c, and a-b-c.

To assist with describing the nanoparticulate material in accordance with the invention, reference is made to FIG. 1. FIG. 1 illustrates a schematic drawing of nanoparticulate material in accordance with the invention (10). The nanoparticulate material per se (20) is represented by an iron oxide nanoparticulate material. Bound to the surface of the nanoparticulate material (20) is (i) a copolymeric mapping moiety represented collectively by features (30), (40) and (50), and (ii) a copolymeric steric stabiliser represented collectively by features (30) and (60). The copolymeric mapping moiety includes an anchoring polymer segment (30) and a coupling polymer segment (40), where the anchoring polymer segment and coupling polymer segment are different. The coupling polymer segment (40) has coupled to it one or more mapping groups (50). The copolymeric steric stabiliser includes an anchoring polymer segment (30) coupled to a steric stabilising polymer segment (60), where the anchoring polymer segment (30) is different to the steric stabilising polymer segment (60). The coupling polymer segment (40) contains more polymerised monomer residue units than the steric stabilising polymer segment (60) thereby enabling the one or more mapping groups (50) to extend a greater distance from the surface of the nanoparticulate material (20) relative to the steric stabilising polymer segment (60).

By the particulate material being "nano" particulate material is meant at least one of its dimension is less than 100 nm, or less than about 75 nm, or less than about 50 nm, or less than about 30 nm. In one embodiment, all dimensions of the nanoparticulate material are less than 100 nm, or less than about 75 nm, or less than about 50 nm, or less than about 30 nm.

The nanoparticulate material may be in the form of primary particles, or in the form or an aggregation of primary particles. In one embodiment, they are in the form of primary particles.

For avoidance of any doubt, reference herein to the "size" of the nanoparticulate material is intended to denote an average size (at least about 50 number %) of the particles based on the largest dimension of a given particle.

The size of the nanoparticulate material per se is determined herein by Transmission Electron Microscopy (TEM).

For avoidance of any doubt, when the nanoparticulate material is in the form of an aggregation of primary particles, reference to the size of such material is intended to be a reference to the largest dimension of the aggregate not the primary particles that form the aggregate.

In certain embodiments, the nanoparticulate material has a size of less than about 50 nm in at least one or all dimensions. In certain embodiments, the nanoparticulate material is of a size that ranges from about 5 nm to about 30 nm, or about 5 nm to about 20 nm, or about 8 nm nm to about 15 nm in at least one or all dimensions.

In one embodiment, nanoparticulate material is of size that is about: 6, 8, 10, 15, 20, 30, 40, 50, 60, 70, 80, 90 or 100 nm.

The nanoparticulate material will typically at least have an outer surface that is solid at temperatures typically experienced in its intended application. Taking into account temperatures that may be experienced by the nanoparticulate material or compositions during use and storage prior to use in their intended application, at least the outer surface of the nanoparticulate material will generally be in a solid state up to at least about 40° C., preferably about 50° C. The nanoparticulate material may of course, and in some embodiments does, have such a solid state composition throughout (i.e. is solid nanoparticulate material).

Apart from having medicinal or diagnostic utility, there is no particular limitation on composition of the nanoparticulate material. The nanoparticulate material may have an organic composition or an inorganic composition or a combination thereof. The nanoparticulate material may be selected from or comprise a pharmaceutically active compound (e.g. a drug), a metal, a metal alloy, a metal salt, a metal complex, a metal oxide, a radioactive isotope, a luminescent compound or group and/or combinations thereof.

Suitable nanoparticulate material may comprise gold, silver and salts, complexes or oxides thereof, calcium carbonate, barium sulphate, bismuth sulphide, iron, iron oxide, chromium oxide, cobalt oxide, manganese oxide, iron oxyhydroxide, chromium oxyhydroxide, cobalt oxyhydroxide, manganese oxyhydroxide, chromium dioxide, other transition metal oxides, radioactive isotopes selected from Auger-electron emitters, alpha emitters, positron emitters and beta emitters, and combinations thereof.

Examples of Auger-electron emitters include $^{51}Cr$, $^{67}Ga$, $^{71}Ge$, $^{75}Se$, $^{77}Br$, $^{80m}Br$, $^{99m}Tc$, $^{103}Pd$, $^{103m}Rh$, $^{111}In$, $^{113m}In$, $^{115m}In$, $^{117m}Sn$, $^{119}Sb$, $^{123}I$, $^{125}I$, $^{131}Cs$, $^{161}Ho$, $^{165}Er$, $^{193m}Pt$, $^{195m}Pt$, $^{201}Tl$, and $^{203}Pb$.

Examples of alpha emitters include $^{211}At$ and $^{213}Bi$.

Examples of beta emitters include: low-energy β emitters such as $^{191}Os$, $^{35}S$, $^{33}P$, $^{45}Ca$, $^{199}Au$, $^{169}Er$, $^{67}Cu$, $^{47}Sc$, $^{177}Lu$, $^{161}Tb$, and $^{105}Rh$; medium-energy β emitters such as $^{131}I$, $^{153}Sm$, $^{77}As$, $^{143}Pr$, $^{198}Au$, $^{159}Gd$, $^{109}Pd$, $^{186}Re$, $^{111}Ag$, and $^{149}Pm$; and high-energy β emitters such as $^{165}Dy$, $^{89}Sr$, $^{32}P$, $^{166}Ho$, $^{188}Re$, $^{114m}In$, $^{142}Pr$, $^{90}Y$, and $^{76}As$.

Examples of radioactive isotopes that may be used in radiation therapy include $^{32}P$, $^{153m}S$, $^{90}Y$, $^{125}I$, $^{192}Ir$, $^{103}Pd$, $^{111}In$, $^{166}Ho$ and $^{213}Bi$.

Examples of radioactive isotopes that may be used as a diagnostic agent include $^{99m}Tc$, $^{67}Ga$, $^{64}Cu$, $^{89}Zr$ and $^{18}F$.

Examples of positron-emitters that may be used as a diagnostic agent include gallium-68, copper-64, zirconium-89, yttrium-86, rubidium-82, scandium-44, multiple isotopes of copper, terbium-182, gallium-66, and cobalt-55.

Where a radioactive isotope is to be used, the radionuclide (s) may be used as the nanoparticulate material per se or may be combined with one or more other suitable nanoparticulate materials. In other words, the nanoparticulate material may comprise one or more radioactive isotopes. For example, $^{67}Ga$ may be used in a form where it is combined with iron oxide particulate material.

In some embodiments, the nanoparticulate material is magnetic. Such magnetic nanoparticulate material may exhibit ferromagnetic, ferrimagnetic or superparamagnetic properties.

In one embodiment, the nanoparticulate material is superparamagnetic.

The nanoparticulate material may be made of or comprise magnetic material.

Examples of suitable magnetic materials include, but are not limited to, iron, nickel, chromium, cobalt, gadolinium, manganese, oxides or oxyhydroxides of any of the aforementioned, and mixtures of any of the aforementioned. In certain embodiments, the magnetic nanoparticles comprises iron and/or an oxide or oxyhydroxide thereof. Suitable iron oxide magnetic materials include maghemite (γ-$Fe_2O_3$) and magnetite ($Fe_3O_4$).

In one embodiment, the magnetic nanoparticulate material comprises one or more of iron, nickel, chromium, cobalt, gadolinium, manganese and oxides or oxyhydroxides thereof.

In another embodiment, the magnetic nanoparticulate material comprise iron (Fe), maghemite (γ-$Fe_2O_3$), magnetite ($Fe_3O_4$) or a combination thereof.

In some embodiments, the magnetic nanoparticulate material are or comprise magnetite ($Fe_3O_4$) or maghemite (γ-$Fe_2O_3$) with a particle size of less than about 30 nm, for example between about 1 and about 20 nm.

The magnetic nanoparticulate material may be in the form of a metal, such as iron, surrounded by a magnetic metal oxide shell, such as a maghemite (γ-$Fe_2O_3$) shell around a core material.

In some embodiments, the magnetic nanoparticulate material is or comprises ferrites of general formula $MO{\cdot}Fe_2O_3$ where M is a bivalent metal such as Fe, Co, Ni, Mn, Be, Mg, Ca, Ba, Sr, Cu, Zn, Pt, Gd or mixtures thereof, or magnetoplumbite type oxides of the general formula $MO{\cdot}6Fe_2O_3$ where M is a large bivalent ion, metallic iron, cobalt or nickel. The magnetic nanoparticulate material may be made up of Fe, Zn, Ni, Cr, Co or Gd or oxides or oxyhydroxides thereof. Alternatively, the magnetic nanoparticulate material could be mixtures of any of those.

In some applications, it may be desirable to use magnetic nanoparticulate material that is superparamagnetic. As used herein, the term "superparamagnetic" is intended to mean magnetic material that does not have the following properties; (i) coercivity, (ii) remanence, or (iii) a hysteresis loop when the rate of change of an applied magnetic field is quasi-static.

In some embodiments, the nanoparticulate material is or comprises luminescent material.

Such luminescent material may be chemiluminescent (e.g. bioluminescent, electrochemiluminescent, candoluminescent, lyoluminescent), electroluminescent, photoluminescent (e.g. fluorescent or phosphorescent), radioluminescent or thermoluminescent. Examples of such luminescent material includes the luminescent groups herein described.

The luminescent material may form all or part of the nano particular material. For example, the luminescent material may be encapsulated within another material so as to form the nanoparticulate material.

The nanoparticulate material according to the invention has bound to its surface copolymeric steric stabiliser that promotes dispersion of the nanoparticulate material in a liquid. That liquid may be a carrier liquid or in vivo liquid as herein described. By "promotes" in that context is meant that in the absence of the copolymeric steric stabiliser the nanoparticulate material would otherwise flocculate, aggregate or settle out from the liquid as sediment. In other words, the copolymeric steric stabiliser functions to maintain the nanoparticulate material in a dispersed state within the liquid.

By being a copolymeric "steric" stabiliser is meant that dispersion of the nanoparticulate material in a liquid occurs as a result of steric repulsion forces. Having said that, the copolymeric steric stabiliser may present electrostatic repulsion forces that also assist with stabilisation of the nanoparticulate material. However, those skilled in the art will appreciate that such electrostatic forces will provide little if any stabilising function in liquids having a relatively high ionic strength. The steric stabilising function of the copolymeric steric stabiliser used in accordance with the invention therefore plays an important role in enabling the nanoparticulate material to be maintained or remain stable in a dispersed state in such liquid.

The copolymeric steric stabiliser used in accordance with the invention has been found to be particularly effective promoting dispersion of the nanoparticulate material in an in vivo liquid environment.

As used herein terms such as "polymeric" or "polymer segment" are intended to be a reference to a polymer chain derived from the polymerisation of monomers. Accordingly, a polymeric component or polymer segment will comprise or be made of polymerised monomer residue units. Such polymeric components or polymer segments can be prepared by any suitable polymerisation technique. In one embodiment, a polymer segment (e.g. anchoring, steric stabilising and coupling) described herein is prepared by the polymerisation of ethylenically unsaturated monomer. The polymer chains may (and some do) have non-polymeric components covalently attached to them, for example mapping or luminescent groups. As used herein the term "copolymeric" is intended to mean a polymer chain that comprises two polymer segments of different composition.

The copolymeric steric stabiliser used in accordance with the invention comprises a steric stabilising polymer segment.

Those skilled in the art will appreciate the variety of polymers that may be employed as the steric stabilising polymer segment, as to the monomers that may be polymerised to form such polymers. The steric stabilising polymer segment may comprise or consist of polyacrylamide (PA), polyvinyl alcohol (PVA), polyalkylene oxide (e.g. polyethylene oxide (PEO), polypropylene oxide (PPO)), polyoxamers, polyhydroxyethylacrylate, poly-N-isopropylacrylamide, polydimethylamino-ethylmethacrylate, polyvinyl pyrrolidone (PVP), polyacrylicacid (PAA), polymethacrylamide, poly vinyl ester, poly vinyl amide, polysulfonateddivinylbenzene, poly-L-lysine, polyaspartate, poly lactic acid, polyethyleneimine, polyalkylcyanoacrylate, polyaspartate, polymaleic anhydride, polymaleic acid, or a copolymer of two or more of the aforementioned. Thus, suitable monomers that may be used to form the steric stabilising polymer segment include, but are not limited to acrylamide, vinyl alcohol, alkylene oxide (e.g. ethylene oxide, propylene oxide), hydroxyethylacrylate, N-isopropylacrylamide, dimethylamino-ethylmethacrylate, vinyl pyrrolidone, acrylic acid, methacrylamide, vinyl ester, vinyl amide, sulfonateddivinylbenzene, L-lysine, aspartate, lactic acid, ethyleneimine, alkylcyanoacrylate, aspartate, maleic anhydride, maleic acid, or a copolymer of two or more of the aforementioned.

Where the steric stabilising polymer segment comprises polyalkylene oxide the polyalkylene oxide may be selected from polyethylene glycol, polypropylene glycol and derivatives thereof. The polyalkylene oxide polymer may be end capped with an alkyl group. The alkyl group may be a $C_1$ to $C_6$ alkyl group, such as a methyl group, an ethyl group, a propyl group or an isopropyl group.

Given the steric stabilising polymer segment forms only part of the copolymeric steric stabiliser, rather than defining the steric stabilising polymer segment in terms of its number average molecular weight, it can instead be useful to make reference to the number of polymerised monomer units that collectively form the segment. Although there is no particular limitation on the number of such units that may collectively form the steric stabilising polymer segment, in some embodiments of the invention it may be desirable that the steric stabilising polymer segment comprise less than about 70 polymerised monomer residue units and, in certain embodiments, has from about 40 to about 60 polymerised monomer residue units, such as about 50 polymerised monomer residue units that make up the overall polymer segment.

In some embodiments, the steric stabilising polymer segment comprises from about 10 to about 70 polymerised monomer residue units.

The steric stabilising polymer segment may be a homopolymer or a copolymer.

In one embodiment, the steric stabilising polymer segment comprises or consists of a polyacrylamide-co-polyalkylene oxide block copolymer. That block copolymer may comprise or consist of about 8 to about 60 polymerised acrylamide units and about 2 to about 10 polymerised alkylene oxide units.

In another embodiment, the steric stabilising polymer segment comprises from about 10 to about 13 polymerised alkylene oxide units.

Those skilled in the art will appreciate polymerised alkylene oxide units provide for poly alkylene oxide.

The polymeric steric stabiliser, polymeric mapping moiety and polymeric luminescent moiety used in accordance with the invention each comprise an anchoring polymer segment.

By an "anchoring polymer segment" is meant a segment or region of the given polymeric entity (i.e. polymeric steric stabiliser, polymeric mapping moiety and polymeric luminescent moiety) that is a polymer chain, has an affinity toward the surface of the nanoparticulate material and functions to secure the given entity to the nanoparticulate material through one or more binding groups. The one or more binding groups may form part of the polymer chain backbone or they may present pendant from the polymer chain backbone. A binding group can be any element or molecule with a binding affinity for the nanoparticulate material. For example, the binding group can be any element or molecule with a binding affinity for iron or iron oxide. Suitable binding groups that can be used include groups comprising one or more phosphorous (P) atom, groups comprising one or more oxygen (O) atom, groups comprising one or more sulfur (S) atom, groups comprising one or more nitrogen (N) atom, and groups comprising any two or more of the aforementioned atoms.

In one embodiment, the anchoring polymer segment comprises one or more binding groups selected from phosphate groups, phosphonate groups, dimercaptosuccinic acid (DMSA) groups, sulfate groups, sulfonate groups, catechol groups, carboxylate groups, amine groups, and silane groups.

By being a polymer segment, it will be appreciated the anchoring polymer segment comprises polymerised monomer residues. In particular, the segment will comprise polymerised monomer residues that give rise to the required binding affinity toward the nanoparticulate material. The polymerised monomer residues that make up the anchoring polymer segment may be the same or different.

It is believed the ability of the anchoring polymer segment to present multiple sites for binding interactions with the nanoparticulate material at least in part gives rise to the excellent stabilising properties provided by the copolymeric steric stabiliser.

The anchoring polymer segment may have at least two polymerised monomer residues that each provides a site for binding with the magnetic nanoparticles, or at least three, or at least five, or at least seven, or at least ten of such polymerised monomer residues. Not all of the polymerised monomer residues that make up the anchoring polymer segment are necessarily required to give rise to a binding interaction with the nanoparticulate material, but it is generally preferred the majority if not all of the polymerised monomer residues that make up the anchoring polymer segment do give rise to a binding interaction with the nanoparticulate material.

The anchoring polymer segment may therefore be described as having multiple sites that collectively secure or bind a given entity to the nanoparticulate material.

To provide the desired anchoring effect, the anchoring polymer segment will have a binding affinity toward the nanoparticulate material. The mode by which an anchoring polymer segment binds to the nanoparticulate material might be by way of electrostatic forces, hydrogen bonding, ionic charge, Van der Waals forces, or any combination thereof. A particular advantage provided by the anchoring polymer segment is that it can provide multiple sites for binding interactions with the nanoparticles. Thus, even where a given binding site only provides a relatively weak interaction with the nanoparticulate material, the presence of multiples of such sites within the segment enables it as a whole to bind securely with the nanoparticulate material.

In one embodiment, the anchoring polymer segment is not covalently bound to the nanoparticulate material.

The anchoring polymer segment required will generally be dictated by the nature of the nanoparticulate material to which it is to bind. Those skilled in the art will be able to select an appropriate anchoring polymer segment to bind with the surface of a given nanoparticulate material.

When describing the interaction of the anchoring polymer segment with the nanoparticulate material, it can be convenient to refer to the hydrophilic and hydrophobic character of the segment and the particulate material. Thus, in general, suitable binding interactions will occur when the segment and the particulate material have similar hydrophilic or hydrophobic character. For example, where the nanoparticulate material has a relatively hydrophilic surface (e.g. its surface can be wetted with an aqueous solution), then good binding should be attained using an anchoring polymeric segment that has hydrophilic character (e.g. in its isolated form the segment would be soluble in an aqueous medium). Such an example might be realised where the particulate material is of a type that can form a charge on its surface. In that case, it may be desirable for the segment to comprise polymerised residues of monomers that can also form a charge (e.g. polymerised residues of an ionisable monomer) so as to promote ionic binding between the segment and the particulate material. Promoting the formation of such charged species might be facilitated by adjusting the pH of the liquid carrier in which the stabiliser and particulate material reside.

By the expression "ionisable monomer" is meant that the monomer comprises a functional group which can be ionised in solution to form a cationic or anionic group. Such functional groups will generally be capable of being ionised under acidic or basic conditions through loss or acceptance of a proton. Generally, the functional groups are acid groups or basic groups (i.e. groups that can donate or accept a H atom, respectively). For example, a carboxylic acid functional group may form a carboxylate anion under basic conditions, and an amine functional group may form a quaternary ammonium cation under acidic conditions. The functional groups may also be capable of being ionised through an ion exchange process.

Those skilled in the art will appreciate the variety of polymers that may be employed as the anchoring polymer segment, as to the monomers that may be polymerised to form such polymers. For example, suitable polymers include, but are not limited to, polyacrylic acid, polymethacrylic acid, polystyrene, polyitaconic acid, poly-p-styrene carboxylic acids, poly-p-styrene sulfonic acids, polyvinyl sulfonic acid, polyvinyl phosphonic acid, poly monoacryloxyethyl phosphate, poly monoacryloxyethyl phosphonic acid, poly-2-(methacryloyloxy)ethyl phosphate, poly-2-(methacryloyloxy)ethyl phosphonic acid, polyethacrylic acid, poly-alpha-chloroacrylic acid, polycrotonic acid, polyfumaric acid, polycitraconic acid, polymesaconic acid, polymaleic acid, poly-2-(dimethyl amino) ethyl and propyl acrylates and methacrylates, the corresponding poly-3-(diethylamino) ethyl and propyl acrylates and methacrylates, polydimethylaminoethylmethacrylate, and copolymers thereof. Thus, suitable monomers that may be used to form the anchoring polymer segment include, but are not limited to, acrylic acid, methacrylic acid, itaconic acid, p-styrene carboxylic acids, p-styrene sulfonic acids, vinyl sulfonic acid, vinyl phosphonic acid, monoacryloxyethyl phosphate, monoacryloxyethylphosphonic acid, 2-(methacryloyloxy) ethyl phosphate, 2-(methacryloyloxy) ethyl phosphonic acid, ethacrylic acid, alpha-chloroacrylic acid, crotonic acid, fumaric acid, citraconic acid, mesaconic acid, maleic acid, 2-(dimethyl amino) ethyl and propyl acrylates and methacrylates, the corresponding 3-(diethylamino) ethyl and propyl acrylates and methacrylates, dimethylaminoethylmethacrylate, and combinations thereof.

The anchoring polymer segment may comprise from about 1 to about 20 phosphonate groups, such as 1 phosphonate group, 2 phosphonate groups, 3 phosphonate groups, 4 phosphonate groups, 5 phosphonate groups, 6 phosphonate groups, 7 phosphonate groups, 8 phosphonate groups, 9 phosphonate groups or 10 phosphonate groups, 11 phosphonate groups, 12 phosphonate groups, 13 phosphonate groups, 14 phosphonate groups, 15 phosphonate groups, 16 phosphonate groups, 17 phosphonate groups, 18 phosphonate groups, 19 phosphonate groups or 20 phosphonate groups. In some embodiments, the anchoring polymer segment may comprise more than 20 phosphonate groups. In certain embodiments, the anchoring polymer segment comprises 5 phosphonate groups.

The anchoring polymer segment may be formed by the polymerisation of one type of monomer or a combination of two or more different monomers. Accordingly, the anchoring polymer segment may be a homopolymer segment or a copolymer segment.

Although there is no particular limitation on the number of polymerised monomer units that collectively form the anchoring polymer segment, in some embodiments of the invention it may be desirable that it has a relatively low number average molecular weight. The anchoring polymer segment may comprise less than about 50, or less than about 40, or less than about 30, or from about 5 to about 25, or from about 5 to about 15 polymerised monomer residue units (that make up the overall segment).

In one embodiment, the anchoring polymer segment comprises 1 to about 30 polymerised monomer residue units.

In one embodiment, the anchoring polymer segment is made up of polymerised residues of one or more ethylenically unsaturated monomers.

The anchoring polymer segment is covalently coupled to either a steric stabilising polymer segment or a coupling polymer segment so as to form the copolymeric steric stabiliser, copolymeric mapping moiety or copolymeric luminescent moiety.

The anchoring polymer segment is different from either the steric stabilising polymer segment or coupling polymer segment thereby affording the copolymer nature of the copolymeric steric stabiliser, copolymeric mapping moiety and copolymeric luminescent moiety.

The polymeric mapping moiety and polymeric luminescent moiety (when used) comprise a coupling polymer segment. The coupling polymer segment is covalently coupled to the anchoring polymer segment. By being a "coupling" polymer segment is meant that it is a polymer chain that links or joins the anchoring polymer segment to either mapping or luminescent groups as described herein. Those mapping or luminescent groups will therefore generally be covalently coupled to the coupling polymer segment. The coupling polymer segment also serves to separate and move the mapping and luminescent groups away from the nanoparticulate material surface to thereby make them more functional, for example in the case of mapping groups more available to receptors on target sites.

Those skilled in the art will appreciate the variety of polymers that may be employed as the coupling polymer segment, as to the monomers that may be polymerised to form such polymers. For example, suitable polymers include, but are not limited to polyacrylamide (PA), polyvinyl alcohol (PVA), polyalkylene oxide (e.g. polyethylene oxide (PEO) and polypropylene oxide (PPO)), polyoxamers, polyhydroxyethylacrylate, poly-N-isopropylacrylamide, polydimethylamino-ethylmethacrylate, polyvinyl pyrrolidone (PVP), polyacrylicacid (PAA), polymethacrylamide, poly vinyl ester, poly vinyl amide, polysulfonateddivinylbenzene, poly-L-lysine, polyaspartate, poly lactic acid, polyethyleneimine, polyalkylcyanoacrylate, polyaspartate, polymaleic anhydride, polymaleic acid, or a copolymer of any of the aforementioned. Thus, suitable monomers that may be used to form the coupling polymer segment include, but are not limited to acrylamide, vinyl alcohol, alkylene oxide (e.g. ethylene oxide and propylene oxide), hydroxyethylacrylate, N-isopropylacrylamide, dimethylamino-ethylmethacrylate, vinyl pyrrolidone, acrylicacid, methacrylamide, vinyl ester, vinyl amide, sulfonateddivinylbenzene, L-lysine, aspartate, lactic acid, ethyleneimine, alkylcyanoacrylate, aspartate, maleic anhydride, maleic acid, and combinations thereof.

In certain embodiments, the coupling polymer segment has less than about 100 polymerised monomer residue units and, in certain embodiments, has from about 30 to about 80 polymerised monomer residue units, or from about 50 to about 80 polymerised monomer residue units, such as about 70 polymerised monomer residue units, that make up the overall polymer segment.

In one embodiment, the coupling polymer segment comprise or consists of polyacrylamide.

In another embodiment, the coupling polymer segment comprises or is made up of about 10 to about 100 polymerised monomer residue units.

In a further embodiment of the coupling polymer segment of one or both of the polymeric mapping moiety and luminescent moiety has more polymerised monomer residue units than the steric stabilising polymer segment. For example, the coupling polymer segment may have at least 2, or at least 4, at least 6, or at least 8, for at least 10, or at least 12, or at least 14, or at least 16, or at least 18, or at least 20 more polymerised monomer residue units than the steric stabilising polymer segment. The coupling polymer segment may have from about 5 to about 70, or about 5 to about 60, or about 5 to about 40, or about 5 to about 20, or about 40 to about 70, or about 50 to about 70 more polymerised monomer residue units than the steric stabilising polymer segment.

Without wishing to be limited by theory, it is believed providing the coupling polymer segment with more polymerised monomer residue units than the steric stabilising polymer segment plays a role in generating a surface environment that is less prone to protein adsorption and subsequent cell uptake in macrophages. That in turn is believed to improve accumulation of the nanoparticulate material in a tumour microenvironment.

Those skilled in the art will be able to select suitable combinations of steric stabilising, anchoring and coupling polymer segments for use with a given nanoparticulate material in order to provide the required function of those respective polymer segments.

The copolymeric mapping moiety and copolymeric luminescent moiety each comprise one or more mapping groups or one or more luminescent groups, respectively. Those mapping and luminescent groups will generally be covalently coupled to the coupling polymer segment of the respective moieties.

The one or more mapping groups as described herein comprise an agent that specifically binds to fibroblast activation protein (FAP).

"Fibroblast activation protein" or "FAP" is a cell surface-expressed proteolytic enzyme that acts on various hormones and extracellular matrix components. Structurally, FAP consists of a six amino acid cytoplasmic tail, a single 20 amino acid transmembrane domain, and a 734 amino acid extracellular domain.

FAP is expressed during development, only rarely in healthy adult tissues. In contrast, FAP is highly upregulated in a wide variety of cancers and in cells of the tumour microenvironment.

The one or more mapping groups comprising an agent that specifically binds to FAP will thus be capable of selectively binding tumour-associated stromal cells in the subject upon administration of the coated nanoparticles. Suitable mapping groups include fibroblast activated protein inhibitors, peptides, proteins, and antibodies targeted at FAP.

In an embodiment, the agent is selected from the group consisting of a small molecule inhibitor and an antibody, or an antigen-binding fragment thereof.

In an embodiment, the agent is a small molecule inhibitor. In another embodiment, the agent is a FAP inhibitor.

Examples of suitable FAP inhibitors include those with a structure:

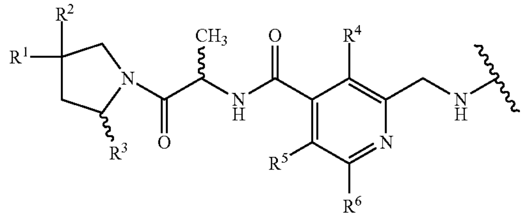

wherein $R^1$ and $R^2$ are the same or different, and are each independently selected from the group consisting of hydrogen, halogen, and $C_1$-$C_4$ alkyl;

$R^3$ is a Ci-C4 alkyl, nitrile, or isonitrile; and $R^4$, $R^5$, and $R^6$ are the same or different, and are each independently selected from the group consisting of hydrogen, halogen, and $C_1$-$C_4$ alkyl.

wherein each of $R^1$ and $R^2$ is a halogen.

wherein each of $R^1$ and $R^2$ is fluorine.

wherein $R^3$ is nitrile.

wherein each of $R^4$, $R^5$, and $R^6$ is hydrogen.

In an embodiment, the agent is an antibody, or an antigen-binding fragment thereof.

Examples of other suitable FAP inhibitors include, but are not limited to, those described in WO2013107820A1, US20200330624A1, EP3763726A1 and U.S. Pat. No. 7,399,869B2.

The term "antibody", as used herein, is understood to mean any antigen-binding molecule or molecular complex comprising at least one complementarity determining region (CDR) that binds specifically to, or interacts specifically with, the target antigen. The term "antibody" includes full-length immunoglobulin molecules comprising two heavy (H) chains and two light (L) chains inter-connected by disulfide bonds, as well as multimers thereof (e.g., IgM). Each heavy chain comprises a heavy chain variable region (which may be abbreviated as HCVR, VH or $V_H$) and a heavy chain constant region. The heavy chain constant region typically comprises three domains—$C_H1$, $C_H2$ and $C_H3$. Each light chain comprises a light chain variable region (which may be abbreviated as LCVR, VL, VK, $V_K$ or $V_L$) and a light chain constant region. The light chain constant region will typically comprise one domain ($C_L1$). The $V_H$ and $V_L$ regions can be further subdivided into regions of hypervariability, termed complementarity determining regions (CDRs), interspersed with regions that are more conserved, also referred to as framework regions (FR). Each $V_H$ and $V_L$ typically comprises three CDRs and four FRs, arranged from amino-terminus to carboxy-terminus in the following order: FR1, CDR1, FR2, CDR2, FR3, CDR3, FR4.

Also, as used herein, an "immunoglobulin" (Ig) hereby is defined as a protein belonging to the class IgG, IgM, IgE, IgA, or IgD (or any subclass thereof), and includes all conventionally known antibodies and functional fragments thereof. A "functional fragment" of an antibody/immunoglobulin is defined as a fragment of an antibody/immunoglobulin (e.g. a variable region of an IgG) that retains the antigen-binding region.

An "antigen-binding region" or "antigen-binding fragment" of an antibody typically is found in one or more hypervariable region(s) of an antibody, i.e. the CDR-1, -2, and/or -3 regions; however, the variable "framework" regions can also play an important role in antigen binding, such as by providing a scaffold for the CDRs. "Functional fragments" include the domain of a $F(ab')_2$ fragment, a Fab fragment, scFv or constructs comprising single immunoglobulin variable domains or single domain antibody polypeptides, e.g. single heavy chain variable domains or single light chain variable domains. The $F(ab')_2$ or Fab may be engineered to minimise or completely remove the intermolecular disulphide interactions that occur between the $C_{H1}$ and $C_L$ domains.

The one or more luminescent group can be any chemical entity that emits electromagnetic radiation or acoustic energy at a desired wavelength following some form of stimulation. The luminescent group may be chemiluminescent (eg. bioluminescent), electroluminescent, photoluminescent, radioluminescent or thermoluminescent. In certain embodiments, the luminescent group is a photoluminescent group that emits light at a specific wavelength following absorption of photons. The photoluminescent group may be fluorescent or phosphorescent.

In certain embodiments, the luminescent group is a fluorescent group belonging to the group of cyanine dyes. Suitable fluorescent groups include indocyanine green (ICG; sodium 4-[2-[(1E,3E,5E,7Z)-7-[1,1-dimethyl-3-(4-sulfonatobutyl)benzo[e]indol-2-ylidene]hepta-1,3,5-trienyl]-1,1-dimethylbenzo[e]indol-3-ium-3-yl]butane-1-sulfonate), IR dyes such as IRdye 800 and sulfocyanine dyes such as sulfo-Cy3, sulfo-Cy5, and sulfo-Cy7. Suitable dyes are available commercially, for example, from Lumiprobe Corporation, Hunt Valley, Maryland, USA.

In one embodiment, the luminescent group is selected from indocyanine green, sulfo-Cy3, sulfo-Cy5, and sulfo-Cy7.

In certain embodiments, the nanoparticulate material has bound to its surface at least one copolymeric steric stabiliser and at least one copolymeric mapping moiety. In other embodiments, the nanoparticulate material has bound to its surface at least one copolymeric steric stabiliser, at least one copolymeric targeting moiety and at least one copolymeric luminescent moiety.

As contemplated herein, the nanoparticulate material or compositions comprising the nanoparticulate material may be used in mapping, diagnostic and/or therapeutic applications.

Accordingly, in an embodiment there is provided a method for mapping a tumour margin in a subject, the method comprising:

a. administering the nanoparticulate material or composition according to the invention to the subject; and
b. detecting the nanoparticulate material, wherein the nanoparticulate material accumulates in the tumour microenvironment, thereby mapping the tumour margin.

The terms "mapping" or "tumour mapping" as used herein refers to the establishment of margins in cancers. Typically, tumour mapping is performed prior to the administration of a treatment for cancer to determine the location and extent of the tumour.

The terms "tumour" and "cancer" as used herein means any condition associated with aberrant cell proliferation. Such conditions will be known to persons skilled in the art. In an embodiment, the tumour is a primary tumour. In another embodiment, the tumour is a solid tumour.

In an embodiment, the cancer is selected from prostate cancer, glioblastoma multiform, glioma, pancreatic cancer, colorectal cancer, breast cancer, head and neck cancer, gastric cancer, oesophageal cancer, ovarian cancer, sarcoma and lung cancer. In another embodiment, the cancer is a prostate cancer.

In an embodiment, the tumour is mapped in situ. The tumour may be mapped in situ before or after tumour tissue resection. In the context of the tumour being mapped after tumour tissue resection, it will be appreciated after tumour tissue resection it is not uncommon to establish, for example through traditional pathology, that the tumour tissue resection has not completely removed all tumour tissue from the subject. The nanoparticulate material according to the present invention advantageously enables tumour mapping to undertaken in situ after tumour tissue resection in order to confirm in real time and without the need for traditional pathology testing all tumour tissue has in fact been resected.

In an embodiment, the nanoparticulate material is detected using an in vivo imaging technique selected from the group consisting of ultrasound, X-ray, optical imaging, Computed Tomography (CT), Single Photon Emission Computed Tomography (SPECT), Positron Emission Tomography (PET), Fluorescence Resonance Energy Transfer (FRET), and Magnetic Resonance Imaging (MRI).

In another embodiment, the method further comprises determining clinical target volume (CTV) and/or gross target volume (GTV) prior to the administration of a treatment.

"Gross tumour volume" or "GTV" refers to the position and extent of gross tumour, i.e., the tumour mass that can be seen, palpated or imaged.

"Clinical target volume" or "CTV" refers to the tumour volume comprising the GTV plus a margin for sub-clinical disease spread. It is generally recognised in the art that the CTV must be adequately treated to achieve cure.

Methods for the calculation of CTV and GTV would be known to persons skilled in the art, illustrative examples of which include the methods described by Burnet et al. (2004, *Cancer Imaging,* 4(2): 153-161).

In another aspect disclosed herein, there is provided a method for the treatment of cancer in a subject in need thereof, the method comprising:

a. administering the nanoparticulate material or composition according to the invention to the subject;
b. detecting a site in the subject where the nanoparticulate material accumulates; and
c. administering an effective amount of a treatment for said cancer at the site of the detected nanoparticulate material in step (b).

The therapeutic regimen for the treatment of cancer can be determined by a person skilled in the art and will typically depend on factors including, but not limited to, the type, size, stage and receptor status of the tumour in addition to the age, weight and general health of the subject. Another determinative factor may be the risk of developing recurrent disease. For instance, for a subject identified as being at high risk or higher risk or developing recurrent disease, a more aggressive therapeutic regimen may be prescribed as compared to a subject who is deemed at a low or lower risk of developing recurrent disease. Similarly, for a subject identified as having a more advanced stage of cancer, for example, stage III or IV disease, a more aggressive therapeutic regimen may be prescribed as compared to a subject that has a less advanced stage of cancer.

The terms "treat", "treatment" and "treating" as used herein refers to any and all uses which remedy a condition or symptom, or otherwise prevent, hinder, retard, abrogate or reverse the onset or progression of cancer or other undesirable symptoms in any way whatsoever. Thus, the term "treating" and the like are to be considered in their broadest possible context. For example, treatment does not necessarily imply that a subject is treated until total recovery or cure. In conditions that display or are characterised by multiple symptoms, the treatment need not necessarily remedy, prevent, hinder, retard, abrogate or reverse all of said symptoms, but may remedy, prevent, hinder, retard, abrogate or reverse one or more of said symptoms.

The subject in which cancer is to be treated may be a human or a mammal of economic importance and/or social importance to humans, for instance, carnivores other than humans (e.g., cats and dogs), swine (e.g., pigs, hogs, and wild boars), ruminants (e.g., cattle, oxen, sheep, giraffes, deer, goats, bison, and camels), horses, and birds including those kinds of birds that are endangered, kept in zoos, and fowl, and more particularly domesticated fowl, e.g., poultry, such as turkeys, chickens, ducks, geese, guinea fowl, and the like, as they are also of economic importance to humans. The term "subject" does not denote a particular age. Thus, adult, juvenile and newborn subjects are intended to be covered.

The terms "subject", "individual" and "patient" are used interchangeably herein to refer to any subject to which the present disclosure may be applicable. In an embodiment, the subject is a mammal. In another embodiment, the subject is a human.

The term "therapeutically effective amount" as used herein means the amount or degree of treatment administered or applied to a subject, in particular a mammal such as a human, in need of such treatment, that is sufficient to treat cancer. The precise amount of treatment to be administered or applied can be determined by a physician with consideration of individual differences in age, weight, tumour size, extent of infection or metastasis, and condition of the subject.

In an embodiment, the treatment is selected from surgery, radiotherapy, brachytherapy, photodynamic therapy, photothermal therapy, focal ablation therapy including cryoablation, focal laser ablation and high-frequency ultrasound ablation, chemotherapy, immunotherapy and combinations thereof.

In an embodiment, the method further comprises determining CTV and/or GTV prior to the administration of the treatment.

In another aspect disclosed herein, there is provided a method for diagnosing cancer, the method comprising:

a. administering the nanoparticulate material or composition according to the invention to a subject; and
b. detecting the nanoparticulate material in the subject;

wherein the detection of accumulated nanoparticulate material in tissue (such as vascular tissue) of the subject indicates that the subject has cancer.

In an embodiment, the detection of accumulated nanoparticulate material in the vascular tissue of the subject indicates that the subject has cancer.

The present invention provides a composition suitable for administration to a subject for use in mapping, diagnostic and/or therapeutic applications, the composition comprising the nanoparticulate material according to the invention dispersed in a pharmacologically acceptable liquid carrier.

On a % wt/wt basis the nanoparticulate material may have bound to its surface various ranges of copolymeric steric stabiliser and copolymeric mapping moiety. For example, the nanoparticulate material may have bound to its surface 10%-90% (wt/wt) of the copolymeric steric stabiliser and 90%-10% (wt/wt) of the copolymeric mapping moiety. In certain embodiments, the nanoparticulate material may have bound to its surface 10% (wt/wt) of the copolymeric steric stabiliser and 90% (wt/wt) of the copolymeric mapping moiety, 15% (wt/wt) of the copolymeric steric stabiliser and 85% (wt/wt) of the copolymeric mapping moiety, 20% (wt/wt) of the copolymeric steric stabiliser and 80% (wt/wt) of the copolymeric mapping moiety, 25% (wt/wt) of the copolymeric steric stabiliser and 75% (wt/wt) of the copolymeric mapping moiety, 30% (wt/wt) of the copolymeric steric stabiliser and 70% (wt/wt) of the copolymeric mapping moiety, 35% (wt/wt) of the copolymeric steric stabiliser and 65% (wt/wt) of the copolymeric mapping moiety, 40% (wt/wt) of the copolymeric steric stabiliser and 60% (wt/wt) of the copolymeric mapping moiety, 45% (wt/wt) of the copolymeric steric stabiliser and 55% (wt/wt) of the copolymeric mapping moiety, 50% (wt/wt) of the copolymeric steric stabiliser and 50% (wt/wt) of the copolymeric mapping moiety, 55% (wt/wt) of the copolymeric steric stabiliser and 45% (wt/wt) of the copolymeric mapping moiety, 60% (wt/wt) of the copolymeric steric stabiliser and 40% (wt/wt) of the copolymeric mapping moiety, 65% (wt/wt) of the copolymeric steric stabiliser and 35% (wt/wt) of the copolymeric mapping moiety, 70% (wt/wt) of the copolymeric steric stabiliser and 30% (wt/wt) of the copolymeric mapping moiety, 75% (wt/wt) of the copolymeric steric stabiliser and 25% (wt/wt) of the copolymeric mapping moiety, 80% (wt/wt) of the copolymeric steric stabiliser and 20% (wt/wt) of the copolymeric mapping moiety, 85% (wt/wt) of the copolymeric steric stabiliser and 15% (wt/wt) of the copolymeric mapping moiety or 90% (wt/wt) of the copolymeric steric stabiliser and 10% (wt/wt) of the copolymeric mapping moiety. In certain specific embodiments, the nanoparticulate material may have bound to its surface 70% (wt/wt) of the copolymeric steric stabiliser and 30% (wt/wt) of the copolymeric mapping moiety.

Those skilled in the art will appreciate the nanoparticulate material according to the invention will present a hydrodynamic diameter when dispersed in a liquid carrier. The hydrodynamic diameter is the distance or size that is derived from the nanoparticulate material per se and at least the copolymeric steric stabilisers and mapping moieties associated with or bound to the nanoparticles. The hydrodynamic diameter of the dispersed nanoparticulate material can therefore be seen to represent the diameter afforded by a combination of the nanoparticulate material per se and at least the copolymeric steric stabilisers and mapping moieties. Where the dispersed nanoparticulate material does not have a symmetrical shape, the hydrodynamic diameter will be considered to be that of the largest hydrodynamic diameter presented by the dispersed nanoparticulate material.

In one embodiment, the hydrodynamic diameter of dispersed nanoparticulate material is less than about 300 nm, less than about 250 nm, less than about 100 nm, less than about 50 nm, less than about 25 nm or less than about 15 nm.

In a further embodiment, the hydrodynamic diameter of dispersed nanoparticulate material is about: 10, 20, 30, 40, 50, 60, 70, 80, 90, 100, 110, 120, 130, 140, 150, 160, 170, 180, 190, 200, 210, 220, 230, 240, 250, 260, 270, 280, 290, or 300 nm.

For avoidance of any doubt, reference herein to the "the hydrodynamic diameter" of dispersed nanoparticulate material is intended to denote an average diameter (at least about 50 number %) of the dispersed coated nanoparticles. The hydrodynamic diameter of dispersed coated nanoparticles is determined herein by dynamic light scattering (DLS).

The nanoparticulate material or composition according to the invention can be used in conjunction with in vivo imaging techniques including, but not limited to, ultrasound, X-ray, optical imaging, Computed Tomography (CT), Single Photon Emission Computed Tomography (SPECT), Positron Emission Tomography (PET), Fluorescence Resonance Energy Transfer (FRET), and Magnetic Resonance Imaging (MRI).

In one application, the nanoparticulate material comprises a FAP targeting group (e.g. inhibitor) and a composition comprising them allows for detection of cells expressing FAP such as cells within the tumour microenvironment (e.g., tumour-associated stromal cells and cancer cells) associated with solid tumours, such as prostate cancer, glioblastoma, pancreatic cancer, colorectal cancer, breast cancer and lung cancer. By specifically binding to FAP expressed by the cells of the tumour microenvironment, the nanoparticulate material is useful for the identification of the boundaries and margins of tissue that is affected by cancer (i.e., tumour mapping). It is also contemplated herein that the nanoparticulate material and compositions may be useful for the detection (i.e., diagnosis) of cancer or as part of the treatment of cancer. For example, the nanoparticulate material may be used for tumour mapping prior to the commencement of treatment, such as focal therapy, radiotherapy, proton therapy or brachytherapy. Furthermore, by accurately mapping the tumour, including regions of the tumour microenvironment, surgical resection of the tumour may be performed with more accuracy to limit undesirable side effects and minimising the risk of suboptimal debulking of the tumour mass.

Unless stated otherwise, the terms "halogen" and "halo" used herein refer to I, Br, Cl and F.

In this specification the term "alkyl", used either alone or in compound words such as "alkenyloxyalkyl", "alkylthio", "alkylamino" and "dialkylamino" denotes straight chain, branched or cyclic alkyl, preferably $C_{1-20}$ alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethyl-propyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2-trimethylpropyl, 1,1,2-trimethylpropyl, heptyl, 5-methoxyhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethyl-pentyl, 1,2,3-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyl-octyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl, 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include mono- or polycyclic alkyl groups such as cyclopropyl, cyclobutyl, cyclopentyl, cyclohexyl, cycloheptyl, cyclooctyl, cyclononyl, cyclodecyl and the like.

EXAMPLES

Example 1: Synthesis of Magnetic Nanoparticles

Part (a) Large maghemite particles were produced using a co-precipitation method. In a typical reaction, $FeCl_2 \cdot 4H_2O$ (20 g) and $FeCl_3 \cdot 6H_2O$ (27 g) in were dissolved in 500 mL of 0.4 M HCl. Ammonia solution (3M, 500 mL) was added to iron salt solution while stirring under an overhead stirrer. The black magnetite nanoparticles formed were magnetically separated and washed with MilliQ water. Magnetite nanoparticles were then oxidised to maghemite by heating in 200 mL of iron(III) nitrate (0.34 M in 1M nitric acid) at 100° C. for 1 hour. The brown maghemite nanoparticles formed were magnetically separated and washed with MilliQ water. The particles were disperse in MilliQ water and dialysed for 2-3 days in Milli-Q water using 14,000 kDa MW cut-off dialysis tube to remove impurities. The particles were analysed by transmission electron microscopy and found to have an average diameter of 16.8±3.3 nm.

Part (b) Small maghemite particles were produced using a co-precipitation method. In a typical reaction, $FeCl_2 \cdot 4H_2O$ (1.46 g) and $FeCl_3 \cdot 6H_2O$ (2.7 g) in were dissolved in 50 mL of 0.4 M HCl. Ammonia solution (3 M, 50 mL) was added to iron salt solution using a syringe pump while stirring under an overhead stirrer. The black magnetite nanoparticles formed were magnetically separated and was washed with MilliQ water. The particles were then oxidised to maghemite using 20 mL of iron(III) nitrate (0.34 M in 1M nitric acid) at 100° C. for 1 hour with stirring. The resulting brown maghemite nanoparticles were magnetically separated and washed with MilliQ water. The particles were dispersed in Milli-Q water and dialysed in Milli-Q water using 14,000 kDa MW cut-off dialysis tube to remove impurities. The particles were analysed by transmission electron microscopy and found to have an average diameter of 12.4±3.2 nm. The particles Z-average diameter was measured by DLS and was found to be 44.5 nm.

Part (c) Magnetite particles were produced using a co-precipitation method. In a typical reaction, $FeCl_2 \cdot 4H_2O$ (1.46 g) and $FeCl_3 \cdot 6H_2O$ (2.7 g) in were dissolved in 2M HCl (10 mL) and MilliQ water (40 mL). Ammonia solution (3 M, 50 mL) was added to iron salts solution using a syringe pump while stirring under an overhead stirrer. The black magnetite nanoparticles formed were magnetically separated and washed with MilliQ water (50 mL) 5 times until a pH of 8.2 was reached for the final particle dispersion. The particles were analysed by transmission electron microscopy and found to have an average diameter of 12.7±3.3 nm.

Example 2 (Comparative): Synthesis of Magnetic Nanoparticles Having Poly{[2-(methacryloyloxy)-ethyl]phosphonic acid}$_5$-block-poly(acrylamide)$_{70}$-(Glu-CO-Lys) polymeric PSMA targeting moiety and poly{[2-(methacryloyloxy)-ethyl]phosphonic acid}$_5$-block-poly(acrylamide)$_{15}$-block-(triethylene glycol monomethyl ether) polymeric steric stabiliser bound thereto (PSMA-targeting nanoparticles)

Part (a): Synthesis of poly{[2-(methacryloyloxy)-ethyl] phosphonic acid}$_5$-block-poly(acrylamide)$_{70}$ 2-(((butylthio)carbonothioyl)-thio)-propanoic acid (0.5 g), acrylamide (10.4 g), 4,4'-azobis(4-cyanovaleric acid) (0.050 g), dioxane (20 g) and water (30 g) were combined in a round bottom flask. The mixture was purged with nitrogen gas, then allowed to react at 70° C. for 3 hours. The solution was allowed to cool to room temperature and [2-(methacryloyloxy)-ethyl]phosphonic acid (2.0 g) and 4,4'-azobis(4-cyanovaleric acid) (0.050 g) were added. The reaction mixture was purged with nitrogen gas and heated to 70° C. for 4 hours. The resulting polymer was precipitated in acetone and collected by vacuum filtration. The polymer was re-purified by dissolving in water, precipitating in acetone and dried in a vacuum oven at 40° C. for 24 hours.

Part (b): Synthesis of poly{[2-(methacryloyloxy)-ethyl] phosphonic acid}$_5$-block-poly(acrylamide)$_{70}$-(Glu-CO-Lys)

Preparation of Glu-CO-Lys. 40 mg of Glu-CO-Lys-(t-Bu)$_3$ Ester was dissolved in 20% trifluoroacetic acid (TFA) in dichloromethane (DCM) to yield a concentration of 20 mg/mL. The mixture was bubbled with nitrogen gas for 2 h at room temperature, after which time the solvents were removed in vacuo. The residue was dissolved in 2 mL 20% aqueous acetic acid and the mixture was washed three times with chloroform, concentrated to dryness under high vacuum resulting in the deprotected Glu-CO-Lys. The product was dissolved in glacial acetic acid, freeze-dried and stored at 4° C. until further use.

Conjugation of Glu-CO-Lys to poly{[2-(methacryloyloxy)-ethyl]phosphonic acid}$_5$-block-poly(acrylamide)$_{70}$. Poly{[2-(methacryloyloxy)-ethyl]phosphonic acid}$_5$-block-poly(acrylamide)$_{70}$ of Part (a) (250 mg), N-(3-Dimethylaminopropyl)-N'-ethylcarbodiimide hydrochloride (EDC.HCl, 60 mg) and N-Hydroxysuccinimide (NHS, 12 mg) were dissolved in 8 mL MES buffer (100 mM, pH 5.5-6.0). The mixture was sonicated in a sonic bath for 10 min followed by precipitation of the NHS-activated polymer in 10 mL acetone. The precipitate was collected by centrifugation for 5 min at 3000 g. Glu-CO-Lys (20 mg) was dissolved in 10× PBS buffer and added to the NHS-activated polymer. The reaction mixture was stirred for 20 hours at room temperature. The Gly-CO-Lys-conjugated polymer was purified using a centrifugal filter with a 3 kDa molecular weight cut off membrane and washed 3 times with water. The product was diluted to a final concentration of 50 mg/mL and stored at 4° C. for further use.

Part (c): Synthesis of poly{[2-(methacryloyloxy)-ethyl] phosphonic acid}$_5$-block-poly(acrylamide)$_{15}$-block-(triethylene glycol monomethyl ether)

Figure 2:
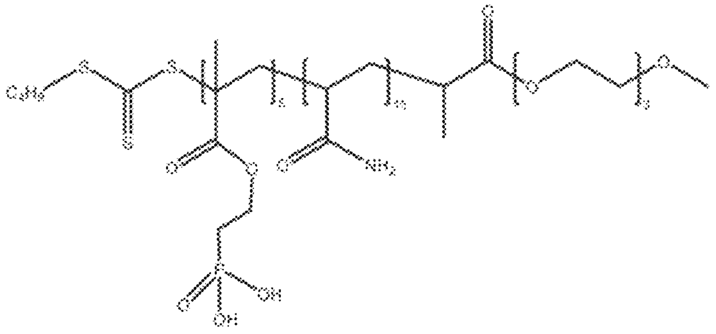
FIG. 2 shows a chemical structure of "long" copolymeric steric stabiliser according the invention.

A solution of acrylamide (2.8 g), 4,4'-azobis(4-cyanovaleric acid) (0.050 g), methoxy triethylene glycol modified 2-{[butylsulfanyl)cabonothioyl]sulfanyl}propanoic acid (1.0 g), dioxane (10 g) and water (10 g) was prepared in a round bottom flask. The mixture was purged with nitrogen gas for 15 minutes and then heated to 70° C. for 2 hours with stirring. The mixture was allowed to cool to room temperature and [2-(methacryloyloxy)-ethyl]phosphonic acid (2.6 g) and 4,4'-azobis(4-cyanovaleric acid) (0.050 g) were added. The reaction mixture was purged with nitrogen gas for 15 min and heated to 70° C. for 4 hours. The resulting polymer was precipitated in acetone and collected by vacuum filtration. The polymer was re-purified by dissolving in water, precipitating in acetone and dried in a vacuum oven at 40° C. for 24 hours. The chemical structure of the polymer is shown in FIG. 2.

Part (d): Particle stabilisation using a mixture of 30% poly{[2-(methacryloyloxy)-ethyl]phosphonic acid}$_5$-block-poly(acrylamide)$_{70}$-(Glu-CO-Lys) and 70% poly{[2-(methacryloyloxy)-ethyl]phosphonic acid}$_5$-block-poly(acrylamide)$_{15}$-block-(triethylene glycol monomethyl ether)

Poly{[2-(methacryloyloxy)-ethyl]phosphonic acid}$_5$-block-poly(acrylamide)$_{15}$-block-(triethylene glycol monomethyl ether) prepared in Part (c) (36 mg) and poly{[2-(methacryloyloxy)-ethyl]phosphonic acid}5-block-poly(acrylamide)$_{70}$-(Glu-CO-Lys) of Part (b) (40 mg) were dissolved in 2 mL of water. The pH was adjusted to 4 using NaOH (0.1 M). The magnetic particles of Example 1[00204] (7 wt % solids, 1 g) were added to the polymer mixture under sonication. The pH was adjusted to 5.5 after 10 min and then to 7.0 after another 10 min of sonication. The sonication was continued for a total of 30 min, after which time the unbound polymers were removed using a centrifugal filter with a 100 kDa molecular weight cut off membrane. The coated nanoparticles were washed 3 times with water and diluted with saline to give an isotonic dispersion at 30 mg Fe/mL.

Figure 3:
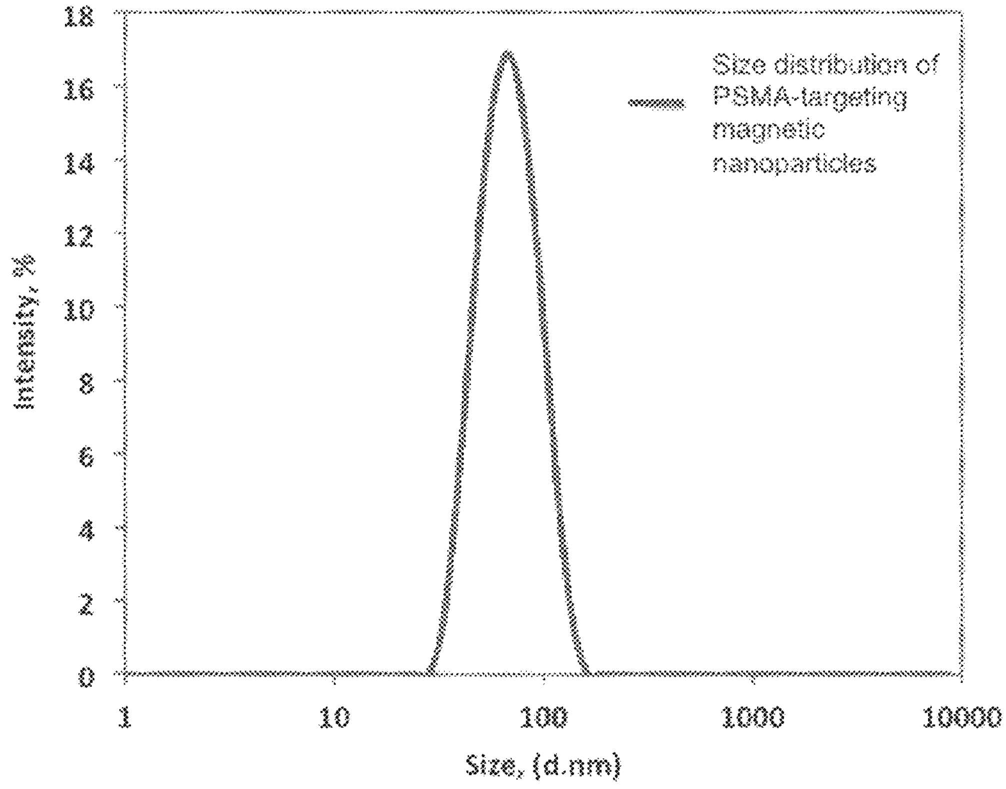
FIG. 3 shows results of a dynamic light scattering (DLS) measurement of a dispersed nanoparticulate material having bound to its surface a prostate specific membrane antigen (PSMA) targeting group.

The z-average of the dispersed nanoparticles measured by DLS in 0.9% saline as the suspending medium was 64.2 nm. The intensity size distribution is shown in FIG. 3.

Example 3: Synthesis of Magnetic Nanoparticles Having poly{[2-(methacryloyloxy)-ethyl]phosphonic acid}$_5$-block-poly(acrylamide)$_{70}$-FAPI copolymeric mapping moiety and poly{[2-(methacryloyloxy)-ethyl]phosphonic acid}$_5$-block-poly(acrylamide)$_{15}$-block-(triethylene glycol monomethyl ether) copolymeric steric stabiliser bound thereto (FAP-mapping nanoparticles)

Part (a): Synthesis of poly{[2-(methacryloyloxy)-ethyl] phosphonic acid}$_5$-block-poly(acrylamide)$_{70}$-FAPI.

Figure 4:
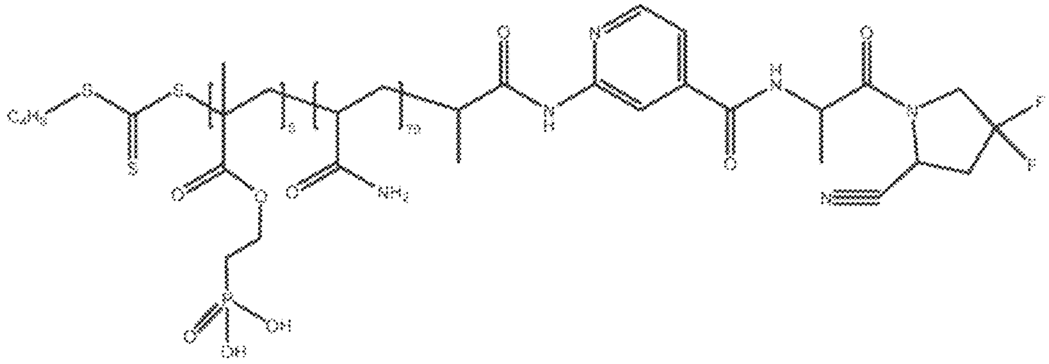
FIG. 4 shows a chemical structure of "long" copolymeric mapping moiety according the invention.

Poly{[2-(methacryloyloxy)-ethyl]phosphonic acid}$_5$-block-poly(acrylamide)$_{70}$ of Example 2-Part (a) (50 mg), EDC.HCl (12 mg) and NHS (3 mg) were dissolved in 2 mL MES buffer (100 mM, pH 5.5-6.0). The solution was sonicated in a sonic bath for 10 min followed by precipitation of the NHS-activated polymer in 6 mL of acetone. The precipitate was collected by centrifugation for 5 min at 3000 g. FAPI (3 mg) was dissolved in 50 μL DMSO and further diluted to a total volume of 2 mL with 10× PBS buffer before addition to the NHS-activated polyacrylamide polymer. The reaction mixture was stirred for 20 hours at room temperature. The FAPI-conjugated polymer was purified using a centrifugal filter with a 3 kDa molecular weight cut off membrane and washed 3 times with water. The product was diluted to a final concentration of 50 mg/mL and stored at 4° C. for further use. The chemical structure of the polymer is shown in FIG. 4.

Part (b): Particle stabilisation using a mixture of 30% poly{[2-(methacryloyloxy)-ethyl]phosphonic acid}$_5$-block-poly(acrylamide)$_{70}$-FAPI copolymeric mapping moiety and 70% poly{[2-(methacryloyloxy)-ethyl]phosphonic acid}$_5$-block-poly(acrylamide)$_{15}$-block-(triethylene glycol monomethyl ether) copolymeric steric stabiliser 18 mg of poly{[2-(methacryloyloxy)-ethyl]phosphonic acid}$_5$-block-poly(acrylamide)$_{15}$-block-(triethylene glycol monomethyl ether) of Example 2-Part (c) and 20 mg of poly{[2-(methacryloyloxy)-ethyl]phosphonic acid}$_5$-block-poly(acrylamide)$_{70}$-FAPI prepared in Part (a) were dissolved in 2 mL of water. The pH was adjusted to 4 with NaOH (0.1 M). The polymer mixture was added to the magnetic particles of Example 1 Part (a) (35 mg) under sonication. The pH was adjusted to 5.5 after 10 min and then to 7.0 after another 10 min of sonication. The sonication was continued for a total of 30 min, after which time the unbound polymers were removed using a centrifugal filter with a 100 kDa molecular weight cut off membrane. The coated nanoparticles were washed 3 times with water and diluted with saline to give an isotonic dispersion at 30 mg Fe/mL.

Figure 5:
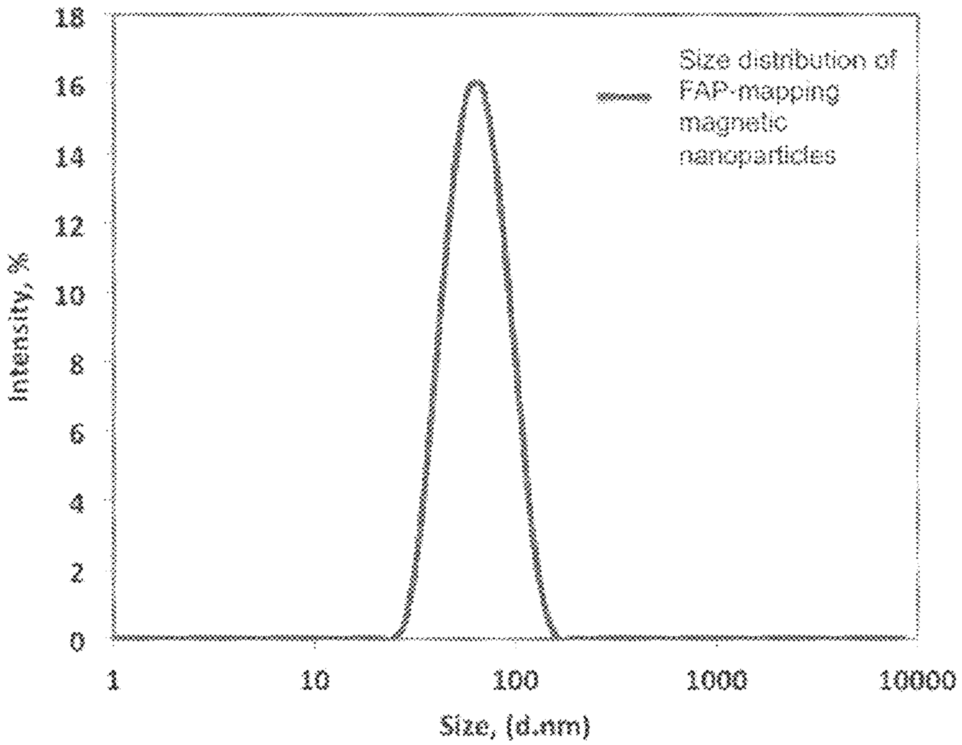
FIG. 5 shows results of a dynamic light scattering (DLS) measurement of a dispersed nanoparticulate material having bound to its surface a fibroblast activation protein inhibitor (FAPI) targeting group.

The z-average of the dispersed nanoparticles measured by DLS in 0.9% saline as the suspending medium was 59.7 nm. The intensity size distribution is shown in FIG. 5.

Part (c) Particle stabilisation for non-targeting particles used as controls using a mixture of 30% poly{[2-(methacryloyloxy)-ethyl]phosphonic acid}$_5$-block-poly(acrylamide)$_{70}$ copolymeric non-targeting moiety and 70% poly{[2-(methacryloyloxy)-ethyl]phosphonic acid}$_5$-block-poly(acrylamide)$_{15}$-block-(triethylene glycol monomethyl ether) copolymeric steric stabiliser (non-targeting nanoparticles).

Figure 6:
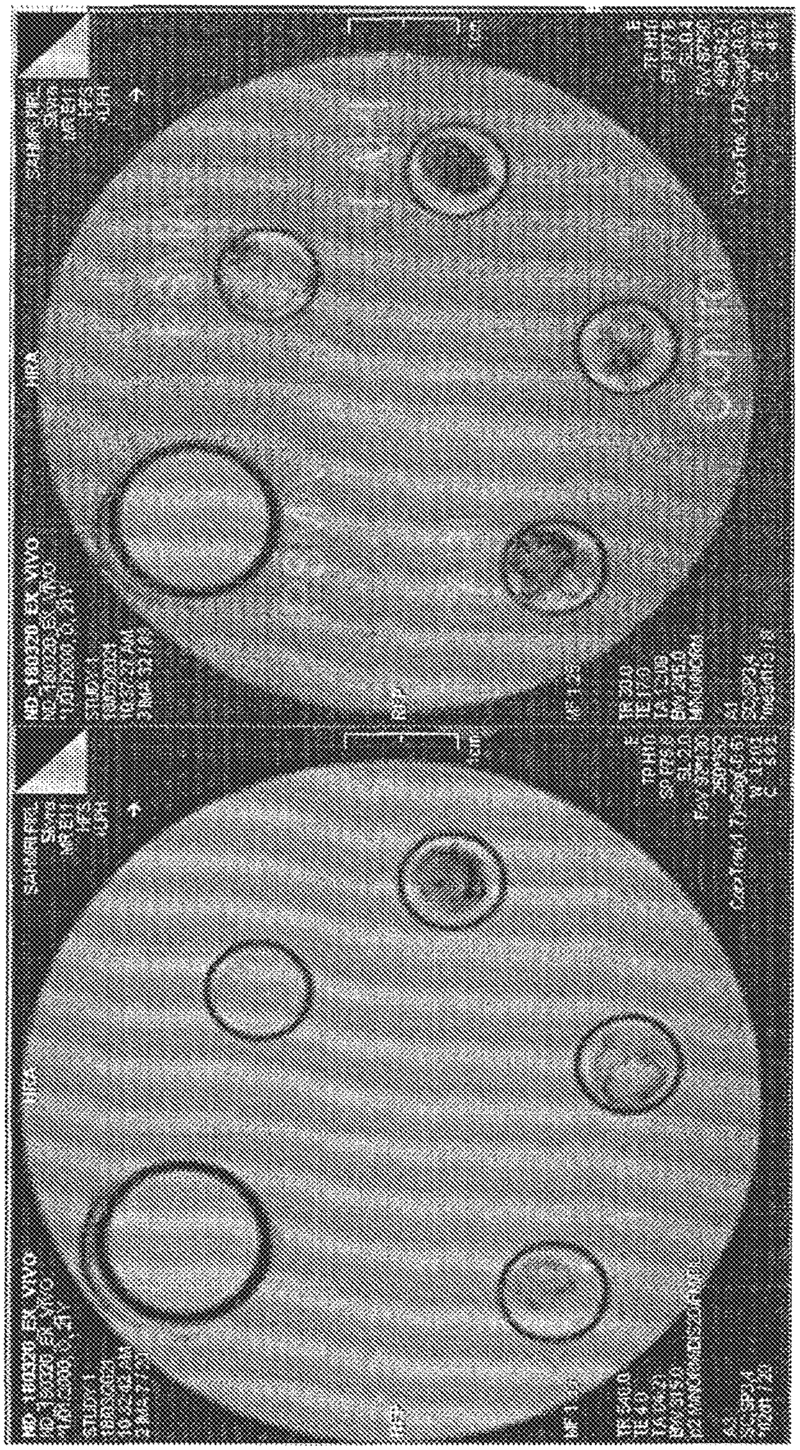
FIG. 6 shows the 3T MRI response of excised orthotopic prostate tumour specimens demonstrating the nanoparticulate material according to the invention with a strong MRI response, versus a weak MRI response from comparative nanoparticulate material shown in FIG. 5[VM1]

18 mg of poly{[2-(methacryloyloxy)-ethyl]phosphonic acid}$_5$-block-poly(acrylamide)$_{15}$-block-(triethylene glycol monomethyl ether) of Example 2 Part (c) and 20 mg of poly{[2-(methacryloyloxy)-ethyl]phosphonic acid}$_5$-block-poly(acrylamide)$_{70}$ of Example 2 Part (a) were dissolved in 2 mL of water. The pH was adjusted to 4 with NaOH (0.1 M). The polymer mixture was added to the magnetic particles of Example 1 Part (a) (35 mg) under sonication. The pH was adjusted to 5.5 after 10 min and then to 7.0 after another 10 min of sonication. The sonication was continued for a total of 30 min, after which time the unbound polymers were removed using a centrifugal filter with a 100 kDa molecular weight cut off membrane. The coated nanoparticles were washed 3 times with water and diluted with saline to give an isotonic dispersion at 30 mg Fe/mL Example 4: Animal Testing Using Tracer for the Delineation of Prostate Tumours Male NOD scid gamma mice aged 6-8 weeks were injected with human prostate cancer cells (LNCaP) directly into the prostate. After 4-6 weeks of tumour growth, the mice were injected with 40 mg/kg of 15 mg/ml of magnetic nanoparticles with PSMA or FAP targeting moiety (prepared in Example 2—Part (d) and Example 3—Part (b), respectively), or no targeting moiety (prepared in Example 3—Part (c)), into the tail vein. 24 hours after injection, mice were sacrificed and tissues were collected for analysis. Resected prostate tumours were fixed in 10% neutral-buffered formalin and mounted in 1% agar gel with 2 mM dimeglumine gadopentetate and underwent T2-weighted MRI using a Siemens 3.0T (FIG. 6). Analysis of the mean signal intensity of the tumours indicated that FAP-mapping nanoparticles provided a 71% increased contrast relative to the nanoparticles with no mapping moiety. PSMA-targeting nanoparticles provided only an 18% increased contrast relative to the nanoparticles with no targeting moiety.

Figure 7:
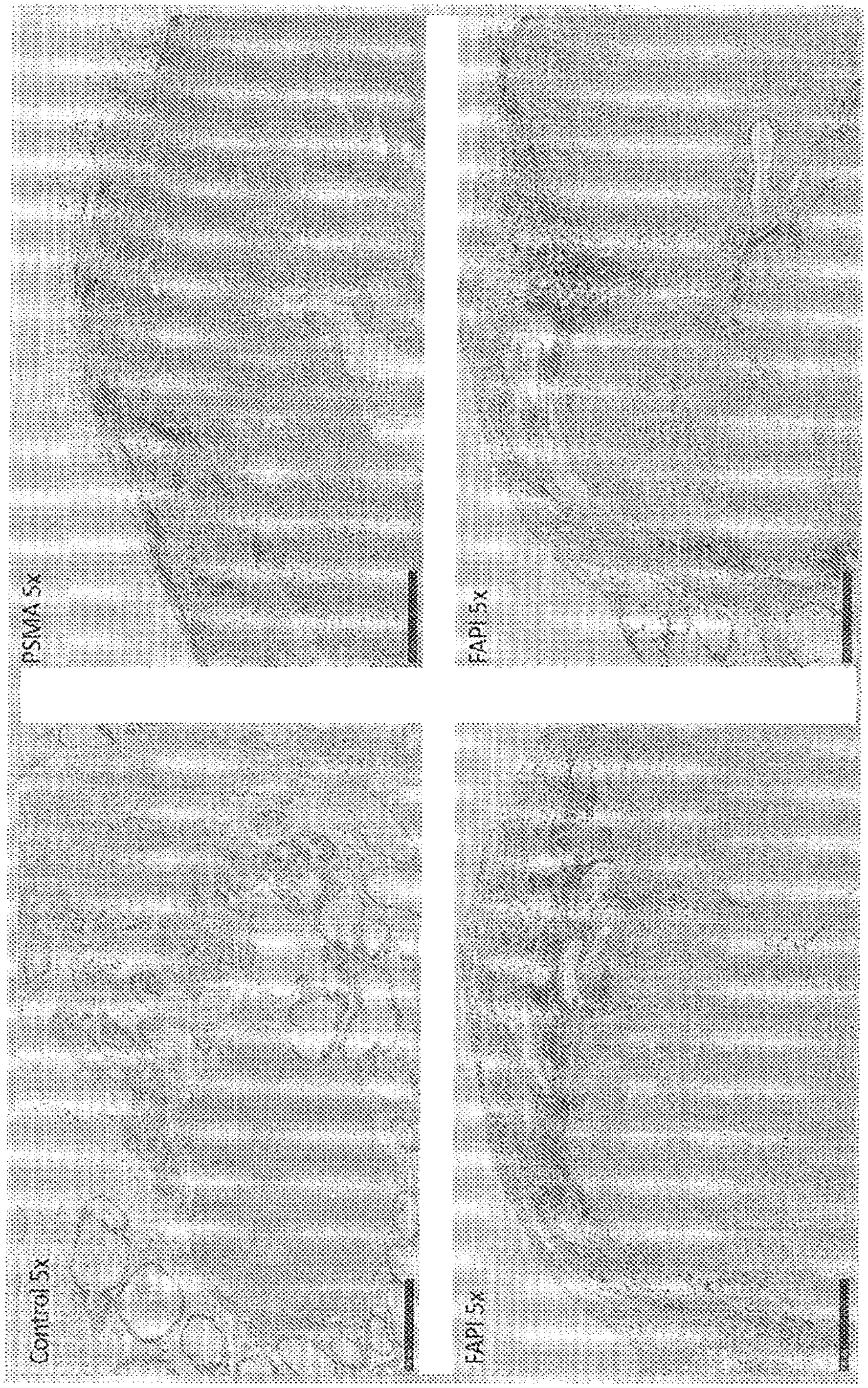
FIG. 7 shows the pathology slides from excised orthotopic tumour specimens demonstrating the nanoparticulate material according to the invention with a strong Prussian blue iron stain on the tumour surface versus the comparative nanoparticulate material shown in FIG. 5 with an iron blue stain showing significantly less nanoparticles at the tumour surface than the nanoparticulate material according to the invention.

Resected prostate tumours fixed in 10% neutral-buffered formalin were mounted in paraffin blocks. 5 μm thick sections were cut and stained with Prussian Blue to visualize the presence of iron nanoparticles (indicated by dark blue staining, 5× magnification, FIG. 7). Mice injected with PSMA-targeting or FAP-mapping nanoparticles showed increased staining for iron, in contrast to the mice injected with nanoparticles with no mapping/targeting moiety which showed minimal staining. On visual inspection, tumours of mice injected with FAP-mapping particles showed increased iron staining in contrast to PSMA-targeting nanoparticles. It was noted FAP-mapping nanoparticles had been taken up particularly around the boundary of the tumour and along the vasculature.

Figure 8:
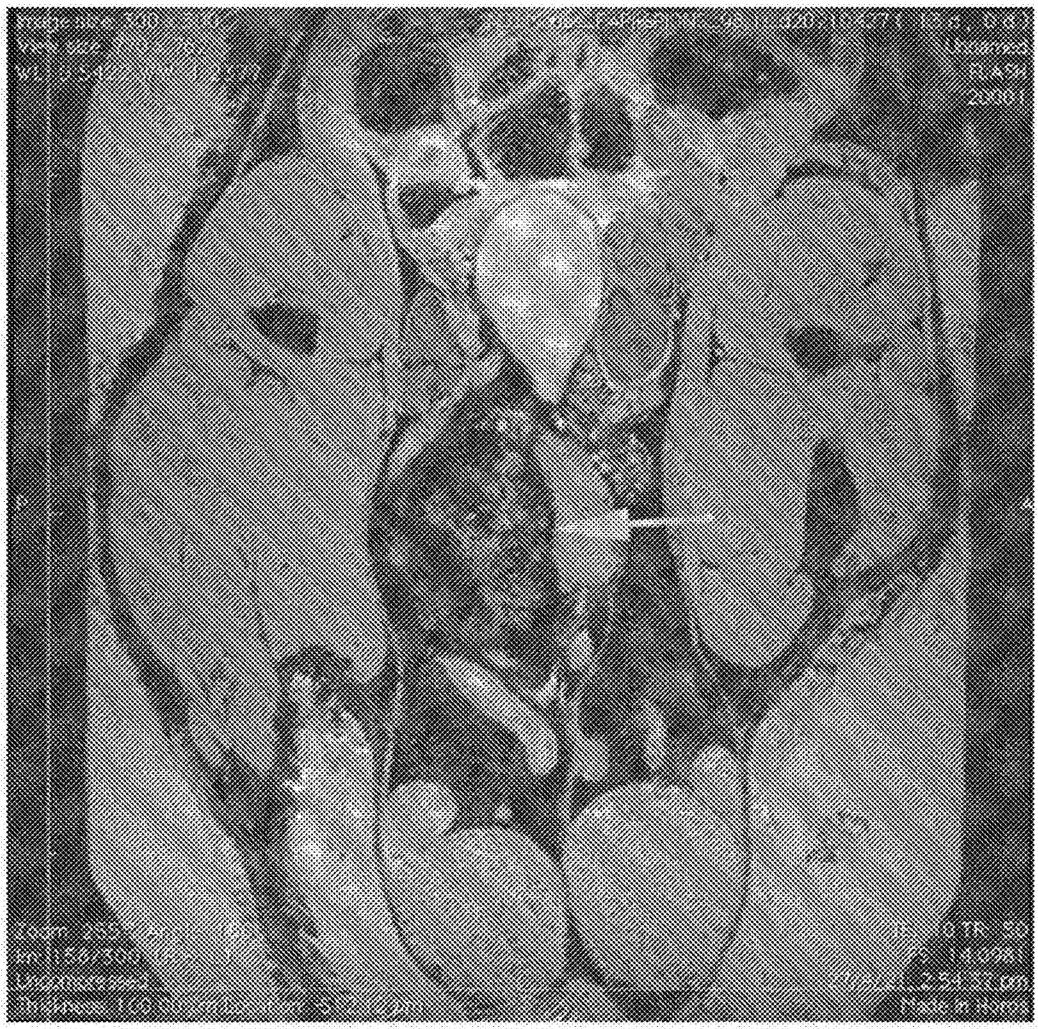
FIG. 8 shows a whole body mouse 14.7T MRI with a negative contrast of the nanoparticulate material according to the invention at the surface of the orthotopic prostate model.

After a 24-hour nanoparticle uptake period, mice were intraperitoneally injected with pentobarbital and were transcardially perfused fixed with 10% neutral buffered formalin. Whole fixed mice underwent T2-weighted MRI scans using a Bruker 14.1T system (FIG. 6). Tumours of mice injected with FAP or PSMA-based nanoparticles showed hypointense regions/increased negative contrast in prostate tumours, particularly on the tumour periphery (tumour indicated by white arrow, FIG. 8).

Example 5: Synthesis of Maghemite Nanoparticles Having Short poly{[2-(methacryloyloxy)-ethyl]phosphonic acid}$_5$-block-poly(acrylamide)$_{30}$-FAPI copolymeric mapping moiety and short poly{[2-(methacryloyloxy)-ethyl]phosphonic acid}$_5$-block-poly(acrylamide)$_{10}$-block-(triethylene glycol monomethyl ether) copolymeric steric stabiliser bound thereto using small maghemite core particles from Example 1 Part (b) (small maghemite FAP-mapping nanoparticles)

Part (a): Synthesis of short poly{[2-(methacryloyloxy)-ethyl]phosphonic acid}$_5$-block-poly(acrylamide)$_{30}$ 2-(((butylthio)carbonothioyl)-thio)-propanoic acid (0.2 g), acrylamide (1.8 g), 4,4'-azobis(4-cyanovaleric acid) (0.020 g), dioxane (3.6 mL) and water (4 mL) were combined in a round bottom flask. The mixture was purged with nitrogen gas, then allowed to react at 70° C. for 2.5 hours. The solution was allowed to cool to room temperature and [2-(methacryloyloxy)-ethyl]phosphonic acid (0.489 g) and 4,4'-azobis(4-cyanovaleric acid) (0.020 g) were added. The reaction mixture was purged with nitrogen gas and heated to 70° C. for 2.5 hours. The resulting polymer was precipitated in acetone and collected by centrifugation. The polymer was re-purified by dissolving in water, precipitating in acetone and dried under vacuum for 48 hours.

Part (b): Synthesis of short poly{[2-(methacryloyloxy)-ethyl]phosphonic acid}$_5$-block-poly(acrylamide)$_{30}$-FAPI.

Figure 9:
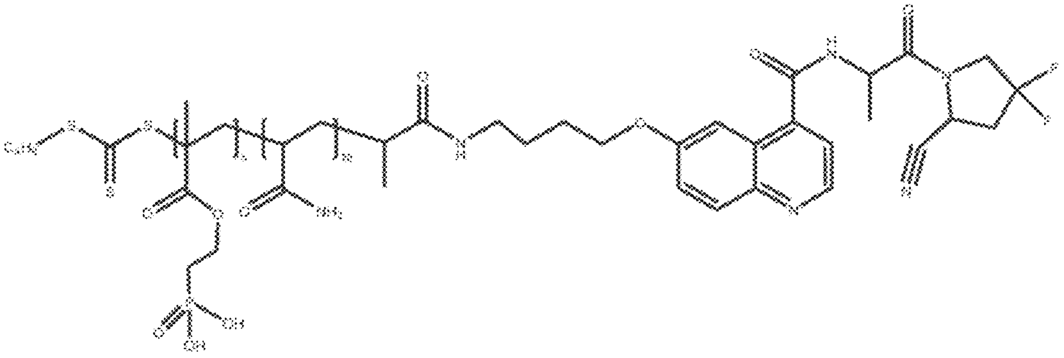
FIG. 9 shows a chemical structure of a "short" copolymeric mapping moiety according the invention.

Poly{[2-(methacryloyloxy)-ethyl]phosphonic acid}$_5$-block-poly(acrylamide)$_{30}$ of Part (a) (150 mg), EDC.HCl (72 mg) and NHS (18 mg) were dissolved in 8 mL MES buffer (100 mM, pH 5.5-6.0). The solution was sonicated in a sonic bath for 10 min followed by removal of the activation solution using a centrifugal filter with a 1 kDa molecular weight cut off membrane. FAPI (18 mg) was dissolved in 50 μL DMSO and further diluted to a total volume of 8 mL with 10× PBS buffer before addition to the NHS-activated polyacrylamide polymer. The reaction mixture was stirred for 20 hours at room temperature. The short FAPI-conjugated polymer was purified using a centrifugal filter with a 1 kDa molecular weight cut off membrane and washed 3 times with water. The product was diluted to a final concentration of 50 mg/mL and stored at 4° C. for further use. The chemical structure of the polymer is shown in FIG. 9.

Part (c): Synthesis of short poly{[2-(methacryloyloxy)-ethyl]phosphonic acid}5-block-poly(acrylamide)$_{10}$-block-(triethylene glycol monomethyl ether)

Figure 10:
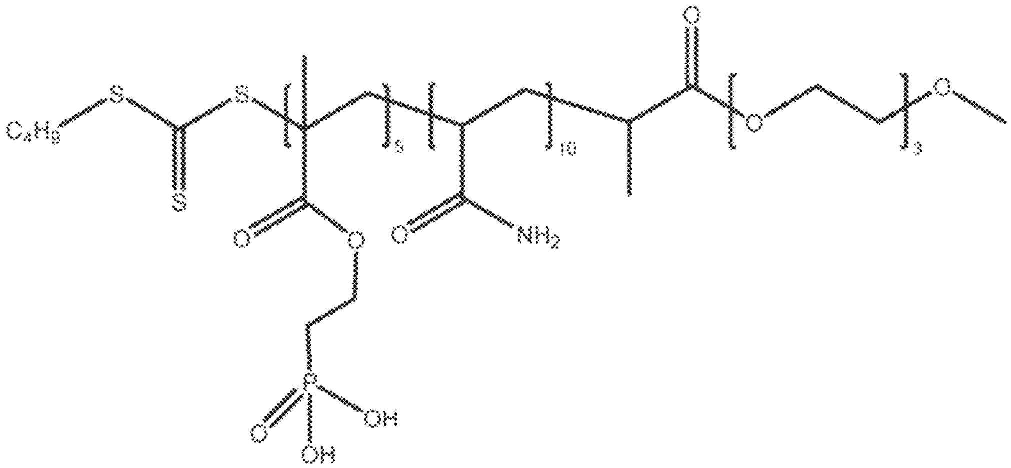
FIG. 10 shows a chemical structure of a "short" copolymeric steric stabiliser according the invention.

A solution of acrylamide (0.93 g), 4,4'-azobis(4-cyanovaleric acid) (0.030 g), methoxy triethylene glycol modified 2-{[butylsulfanyl)cabonothioyl]sulfanyl}propanoic acid (0.5 g), dioxane (7 mL) and water (4 mL) was prepared in a round bottom flask. The mixture was purged with nitrogen gas for 15 minutes and then heated to 70° C. for 1.5 hours with stirring. The mixture was allowed to cool to room temperature and [2-(methacryloyloxy)-ethyl]phosphonic acid (1.2 g) and 4,4'-azobis(4-cyanovaleric acid) (0.030 g) were added. The reaction mixture was purged with nitrogen gas for 15 min and heated to 70° C. for 2 hours. The resulting polymer was precipitated in acetone and collected by centrifugation. The polymer was dried in vacuum over 48 h. The chemical structure of the polymer is shown in FIG. 10.

Part (d): Stabilisation of maghemite nanoparticles using a mixture of 30% short poly{[2-(methacryloyloxy)-ethyl]phosphonic acid}$_5$-block-poly(acrylamide)$_{30}$-FAPI copolymeric mapping moiety and 70% short poly{[2-(methacryloyloxy)-ethyl]phosphonic acid}$_5$-block-poly(acrylamide)$_{10}$-block-(triethylene glycol monomethyl ether) copolymeric steric stabiliser (Tracer 1, 30% FAP-mapping maghemite nanoparticles)

44 mg of poly{[2-(methacryloyloxy)-ethyl]phosphonic acid}$_5$-block-poly(acrylamide)$_{10}$-block-(triethylene glycol monomethyl ether) prepared in Part (c) and 50 mg of poly{[2-(methacryloyloxy)-ethyl]phosphonic acid}$_5$-block-poly(acrylamide)$_{30}$-FAPI prepared in Part (b) were dissolved in 2 mL of water. The pH was adjusted to 4 with NaOH (0.1 M). The polymer mixture was added to 60 mg magnetic particles in water (30 mg/mL) of Example 1 Part (b) under sonication. The pH was adjusted to 5.5 after 10 min and then to 7.0 after another 10 min of sonication. The sonication was continued for a total of 30 min, after which time the unbound polymers were removed using a centrifugal filter with a 10 kDa molecular weight cut off membrane. The coated nanoparticles (Tracer 1) were washed 3 times with water and diluted with saline to give an isotonic dispersion at 20 mg Fe/mL Part (e) Stabilisation of maghemite nanoparticles using 100% short poly{[2-(methacryloyloxy)-ethyl]phosphonic acid}$_5$-block-poly(acrylamide)$_{30}$-FAPI polymeric mapping moiety (Tracer 2, 100% FAP-mapping maghemite nanoparticles).

50 mg of poly{[2-(methacryloyloxy)-ethyl]phosphonic acid}$_5$-block-poly(acrylamide)$_{30}$-FAPI prepared in Part (c) was diluted to a total volume of 2 mL in water. The pH was measured to be 6.9. The polymer was added to 30 mg magnetic particles in water (30 mg/mL) of Example 1 Part (b) under sonication. After the sonication step, the pH was measured to be 5.8. It was subsequently adjusted to 7.0 under sonication using NaOH (0.1 M). The sonication was continued for a total of 20 min, after which time the unbound polymers were removed using a centrifugal filter with a 10 kDa molecular weight cut off membrane. The coated nanoparticles (Tracer 2) were washed 3 times with water and diluted with saline to give an isotonic dispersion at 20 mg Fe/mL.

Part (f) Stabilisation of non-targeting maghemite nanoparticles used as controls using a mixture of 30% short poly{[2-(methacryloyloxy)-ethyl]phosphonic acid}$_5$-block-poly(acrylamide)$_{30}$ copolymeric non-targeting moiety and 70% short poly[2-(methacryloyloxy)-ethyl]phosphonic acid}$_5$-block-poly(acrylamide)$_{10}$-block-(triethylene glycol monomethyl ether) copolymeric steric stabiliser (Tracer 3, non-targeting maghemite nanoparticles).

44 mg of poly{[2-(methacryloyloxy)-ethyl]phosphonic acid}$_5$-block-poly(acrylamide)$_{10}$-block-(triethylene glycol monomethyl ether) prepared in Part (c) and 50 mg of poly{[2-(methacryloyloxy)-ethyl]phosphonic acid}$_5$-block-poly(acrylamide)$_{30}$ prepared in Part (a) were dissolved in 2 mL of water. The pH was adjusted to 4 with NaOH (0.1 M). The polymer mixture was added to 60 mg magnetic particles in water (30 mg/mL) of Example 1 Part (b) under sonication. The pH was adjusted to 5.5 after 10 min and then to 7.0 after another 10 min of sonication. The sonication was continued for a total of 30 min, after which time the unbound polymers were removed using a centrifugal filter with a 10 kDa molecular weight cut off membrane. The coated nanoparticles (Tracer 3) were washed 3 times with water and diluted with saline to give an isotonic dispersion at 20 mg Fe/mL.

Example 6: In-Vitro Testing of the Binding of the Small FAP-Mapping Maghemite Nanoparticles to FAP The binding affinity of 30% FAP-mapping (Tracer 1), 100% FAP-mapping (Tracer 2) and nong-targeting maghemite nanoparticles (Tracer 3) of Example 5 Part (d), (e) and (f), respectively, to the fibroblast activation protein were evaluated in vitro by comparing their cellular uptake in a FAP expressing melanoma cell line C32. C32 cells were cultured in T75 cell culture flasks in RPMI medium supplemented with 10% Fetal Bovine Serum (FBS) and 1% Penicillin-Streptomycin and were kept in a 37° C., 5% $CO_2$ incubator. Cells were passaged when 70-80% confluence was reached. To measure the cellular uptake and test the binding affinity of the nanoparticles, the C32 cells were seeded in a 6 well plate at a density of $3\times10^5$ cells per well in the complete cell culture medium as described above. The plates were placed in a 37° C., 5% $CO_2$ incubator and allowed to adhere for 24 h.

Figure 11:
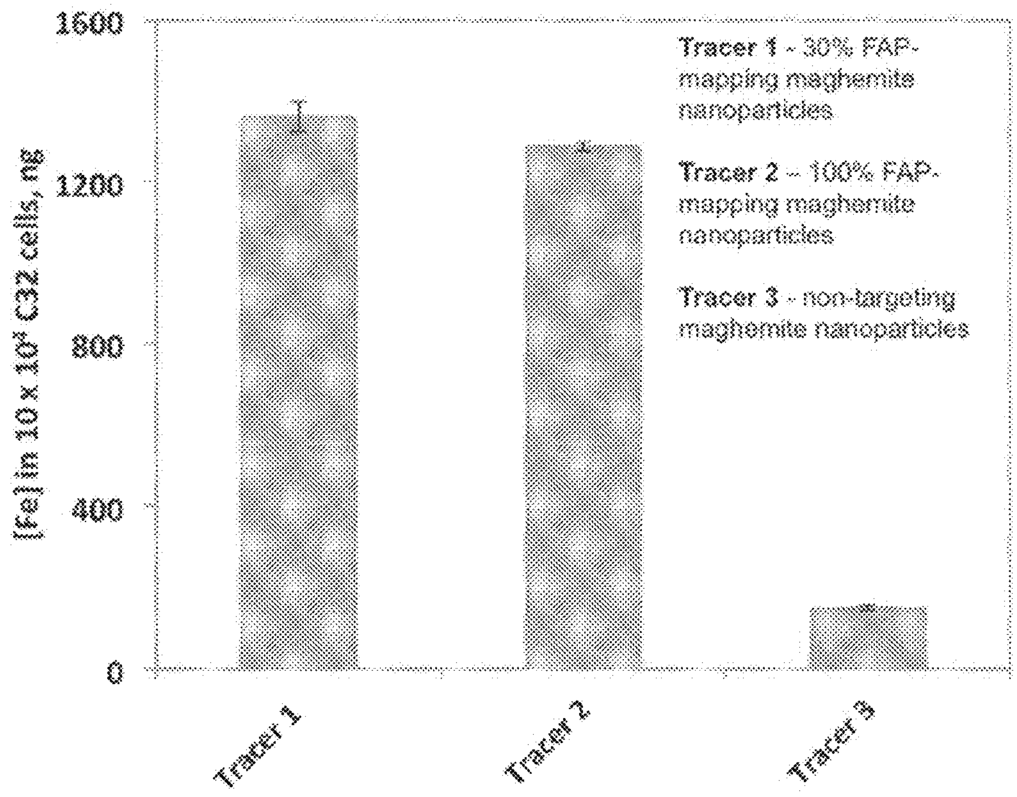
FIG. 11 shows the comparison of cellular uptake of small FAP-mapping magnetic nanoparticles (maghemite) vs non-targeted small magnetic nanoparticles in FAP expressing cell line.

All nanoparticles were prepared at a concentration of 0.150 mg Fe·mL$^{-1}$ in cell culture medium supplemented with 1% Penicillin-Streptomycin only. The growth cell culture media was removed from the plates and replaced by the tracer dispersions. Three replicates were used to test each tracer. C32 cells were incubated with the tracer dispersions for 24 h in a 37° C., 5% $CO_2$ incubator. The cells were washed two times with PBS, detached using trypsin and cell pellets were collected via centrifugation at 500 g for 5 min. The cell pellets were washed two more times with PBS and finally dried at 60° C. overnight using a heating block. The dried cell pellets were digested with trace metal grade nitric and hydrochloric acid (1:1 ratio by volume) and samples were diluted with water to a total volume of 3 mL. Iron concentration was measured with inductively coupled plasma mass spectrometry (ICP-MS). The results showed that Tracer 3 (non-targeting maghemite nanoparticles) had much lower cellular uptake in C32 cells compared to Tracer 1 (30% FAP-mapping maghemite nanoparticles) and Tracer 2 (100% FAP-mapping maghemite nanoparticles), as shown in FIG. 11.

Example 7: In-Vitro Testing of the Binding Activity of the Small Copolymeric FAP-Mapping Maghemite Nanoparticles Vs Single Polymer Small FAP-Mapping Maghemite Nanoparticles in the Presence or Absence of Serum The binding activity of 30% FAP-mapping (Tracer 1), 100% FAP-mapping (Tracer 2) of Example 5 Part (d) and (e), respectively, to the fibroblast activation protein were evaluated in vitro by comparing their cellular uptake in a FAP expressing melanoma cell line C32 in the presence or absence of serum (FBS) in the cell growth media. C32 cells were cultured as described in Example 6. C32 cells were seeded in 6 well plates at a density of $3\times10^5$ cells per well in the complete cell culture medium. The plates were placed in a 37° C., 5% $CO_2$ incubator and allowed to adhere for 24 h.

Figure 12:
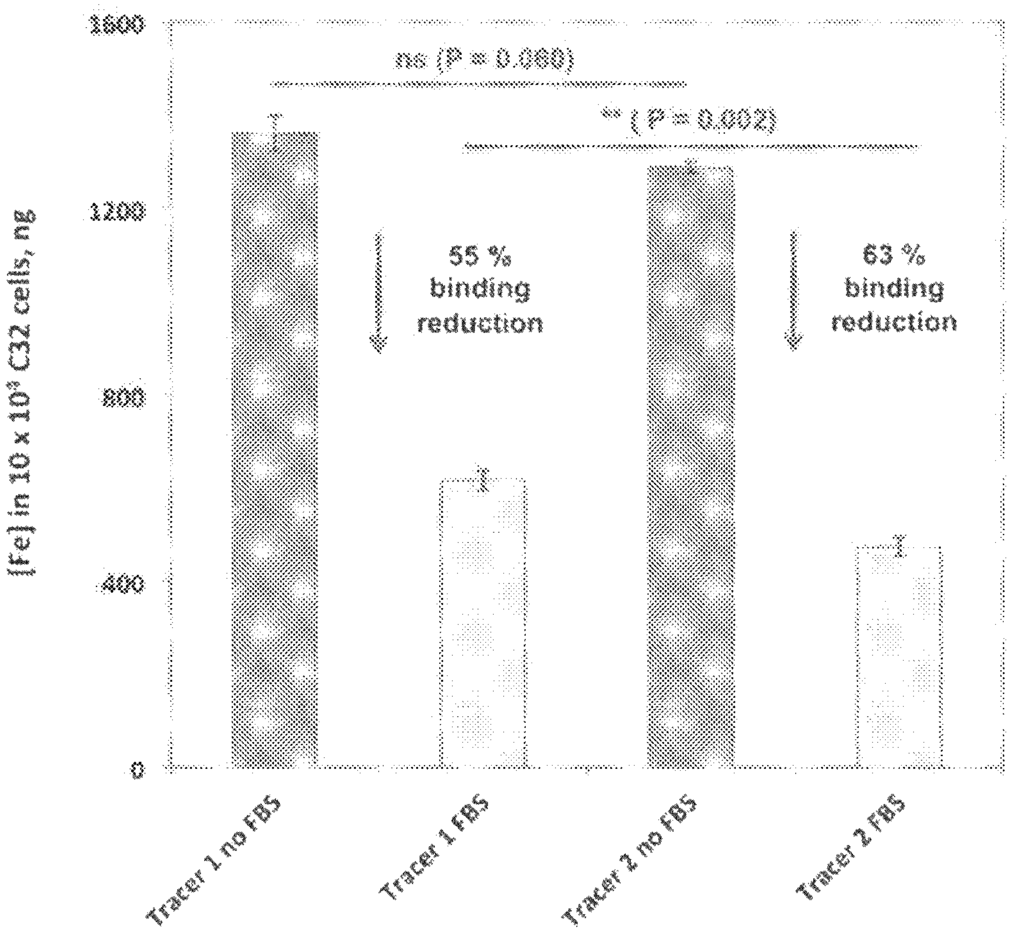
FIG. 12 shows the comparison of cellular uptake of small copolymeric FAP-mapping magnetic nanoparticles (maghemite) vs single polymer FAP-mapping magnetic nanoparticles in FAP expressing cell line in the presence and absence of Fetal Bovine Serum (FBS)

After 24 h the complete cell culture media was removed from one of the 6 well plates and replaced with media supplemented with 1% Penicillin-Streptomycin only. Cell culture media in the other 6 well plate was removed but replaced with media supplemented with 1% Penicillin-Streptomycin and 10% FBS. Nanoparticles of Example 5 Part (d) and (e) were added to each well to a final concentration of 0.150 mg $Fe\cdot mL^{-1}$. C32 cells were incubated with the tracer dispersions for 24 h in a 37° C., 5% $CO_2$ incubator. The cells were washed two times with PBS, detached using trypsin and cell pellets were collected via centrifugation at 500 g for 5 min. The cell pellets were washed two more times with PBS and finally dried at 60° C. overnight using a heating block. The dried cells pellets were digested with trace metal grade nitric and hydrochloric acid (1:1 ratio by volume) and samples were diluted with water to a total volume of 3 mL. Iron concentration was measured with inductively coupled plasma mass spectrometry (ICP-MS). The acquired data was analysed and tested for significance with Independent Sample T-Test. The results presented in FIG. 12 show that there was a significant reduction in binding in the presence of FBS compared to the binding in the absence of FBS for both tracers. However, the binding reduction of Tracer 1 (30% FAP-mapping nanoparticles) was 55%, statistically significantly lower than the 63% binding reduction of Tracer 2 (100% FAP-mapping nanoparticles) ($p<0.01$). The uptakes of Tracer 1 and Tracer 2 in the absence of FBS showed no significant difference ($p>0.05$).

Example 8: Synthesis of Magnetite Nanoparticles Having Short poly{[2-(methacryloyloxy)-ethyl] phosphonic acid}$_5$-block-poly(acrylamide)$_{30}$-FAPI copolymeric mapping moiety and short poly{[2-(methacryloyloxy)-ethyl]phosphonic acid}$_5$-block-poly(acrylamide)$_{10}$-block-(triethylene glycol monomethyl ether) copolymeric steric stabiliser bound thereto using small magnetite core particles from Example 1 Part (c) (small magnetite FAP-mapping nanoparticles)

Part (a): Stabilisation of magnetite nanoparticles using a mixture of 30% short poly{[2-(methacryloyloxy)-ethyl] phosphonic acid}$_5$-block-poly(acrylamide)$_{30}$-FAPI copolymeric mapping moiety and 70% short poly{[2-(methacryloyloxy)-ethyl]phosphonic acid}$_5$-block-poly(acrylamide)$_{10}$-block-(triethylene glycol monomethyl ether) copolymeric steric stabiliser (Tracer 4, 30% FAP-mapping magnetite nanoparticles).

44 mg of poly{[2-(methacryloyloxy)-ethyl]phosphonic acid}$_5$-block-poly(acrylamide)$_{10}$-block-(triethylene glycol monomethyl ether) prepared in Example 5 Part (c) and 50 mg of poly{[2-(methacryloyloxy)-ethyl]phosphonic acid}$_5$-block-poly(acrylamide)$_{30}$-FAPI prepared in Example 5 Part (b) were dissolved in 2 mL of water. The pH was adjusted to 4 with NaOH (0.1 M). The polymer mixture was added to 50 mg magnetic particles in water (25 mg/mL) of Example 1 Part (c) under sonication for 10 min. Prior to adding the polymer mixture, the pH of the nanoparticles was measured to be 7.8. After the sonication step, the pH was measured to be 5.4. It was subsequently adjusted to 6.0 and 7.0 under sonication using NaOH (0.1 M). The sonication was continued for a total of 30 min, after which time the unbound polymers were removed using a centrifugal filter with a 10 kDa molecular weight cut off membrane. The coated nanoparticles (Tracer 4) were washed 3 times with water and diluted with saline to give an isotonic dispersion at 20 mg Fe/mL.

Part (b) Stabilisation of magnetite nanoparticles for non-targeting particles used as controls using a mixture of 30% short poly{[2-(methacryloyloxy)-ethyl]phosphonic acid}$_5$-block-poly(acrylamide)$_{30}$ copolymeric non-targeting moiety and 70% short poly{[2-(methacryloyloxy)-ethyl]phosphonic acid}$_5$-block-poly(acrylamide)$_{10}$-block-(triethylene glycol monomethyl ether) copolymeric steric stabiliser (Tracer 5, non-targeting magnetite nanoparticles).

44 mg of poly{[2-(methacryloyloxy)-ethyl]phosphonic acid}$_5$-block-poly(acrylamide)$_{10}$-block-(triethylene glycol monomethyl ether) prepared in Example 5 Part (c) and 50 mg of poly{[2-(methacryloyloxy)-ethyl]phosphonic acid}$_5$-block-poly(acrylamide)$_{30}$ prepared in Example 5 Part (a) were dissolved in 2 mL of water. The pH was adjusted to 4 with NaOH (0.1 M). The polymer mixture was added to 50 mg magnetic particles in water (30 mg/mL) of Example 1 Part (c) under sonication. Prior to adding the polymer mixture, the pH of the nanoparticles was measured to be 7.8. After the sonication step, the pH was measured to be 5.4. It was subsequently adjusted to 6.0 and 7.0 under sonication using NaOH (0.1 M). The sonication was continued for a total of 30 min, after which time the unbound polymers were removed using a centrifugal filter with a 10 kDa molecular weight cut off membrane. The coated nanoparticles (Tracer 5) were washed 3 times with water and diluted with saline to give an isotonic dispersion at 20 mg Fe/mL.

Example 9: In-Vitro Testing of the Binding of the Small FAP-Mapping Magnetite Nanoparticles to FAP The binding affinity of 30% FAP-mapping magnetite nanoparticles (Tracer 4) versus non-targeting magnetite nanoparticles (Tracer 5) of Example 8 Part (a) and (b) to the fibroblast activation protein were evaluated in vitro by comparing their cellular uptake in a FAP expressing melanoma cell line C32. C32 cells were cultured as described in Example 6. To measure the cellular uptake and test the binding affinity of the nanoparticles, the C32 cells were seeded in a 6 well plate at a density of $3\times10^5$ cells per well in the complete cell culture medium as described above. The plates were placed in a 37° C., 5% $CO_2$ incubator and allowed to adhere for 24 h.

Figure 13:
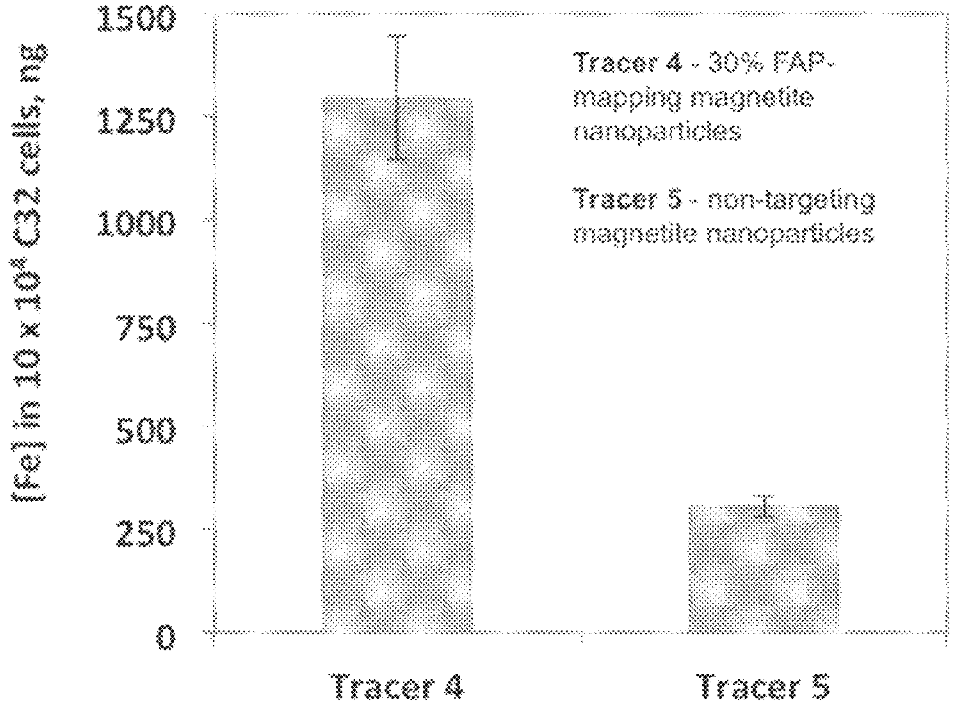
FIG. 13 shows the comparison of cellular uptake of small FAP-mapping magnetic nanoparticles (magnetite) vs non-targeted small magnetic nanoparticles (magnetite) in FAP expressing cell line.

All nanoparticles were prepared at a concentration of 0.150 mg $Fe\cdot mL^{-1}$ in cell culture medium supplemented with 1% Penicillin-Streptomycin and 10% FBS. The cell culture media was removed from the plates and replaced by the tracer dispersions. Four replicates were used to test each tracer. C32 cells were incubated with the tracer dispersions for 24 h in a 37° C., 5% $CO_2$ incubator. The cells were washed two times with PBS, detached using trypsin and cell pellets were collected via centrifugation at 500 g for 5 min. The cell pellets were washed two more times with PBS and finally dried at 60° C. overnight using a heating block. The dried cell pellets were digested with trace metal grade nitric and hydrochloric acid (1:1 ratio by volume) and samples were diluted with water to a total volume of 3 mL. Iron concentration was measured with inductively coupled plasma mass spectrometry (ICP-MS). The results showed that Tracer 5 (non-targeting magnetite nanoparticles) had much lower cellular uptake in C32 cells compared to Tracer 4 (30% FAP-mapping magnetite nanoparticles) as shown in FIG. 13.

It will be appreciated by those skilled in the art that the disclosure is not restricted in its use to the particular application described. Neither is the present disclosure restricted in its preferred embodiment with regard to the particular elements and/or features described or depicted herein. It will be appreciated that the disclosure is not limited to the embodiment or embodiments disclosed, but is capable of numerous rearrangements, modifications and substitutions without departing from the scope of the disclosure as set forth and defined by the following claims.

Throughout the specification and the claims that follow, unless the context requires otherwise, the words "comprise" and "include" and variations such as "comprising" and "including" will be understood to imply the inclusion of a stated integer or group of integers, but not the exclusion of any other integer or group of integers.

The reference to any prior art in this specification is not, and should not be taken as, an acknowledgement of any form of suggestion that such prior art forms part of the common general knowledge.

The invention claimed is:

1. Magnetic nanoparticulate material suitable for administration to a subject, the magnetic nanoparticulate material having bound to its surface:

(a) copolymeric steric stabiliser that promotes dispersion of the magnetic nanoparticulate material in a liquid, wherein the copolymeric steric stabiliser comprises (i) an anchoring polymer segment having one or more binding groups that bind the copolymeric steric stabiliser to the magnetic nanoparticulate material, and (ii) a steric stabilising polymer segment that is different from the anchoring polymer segment, and (b) copolymeric mapping moiety comprising (i) an anchoring polymer segment having one or more binding groups that bind the copolymeric mapping moiety to the magnetic nanoparticulate material, (ii) one or more mapping groups comprising an agent that specifically binds to fibroblast activation protein (FAP), and (iii) a coupling polymer segment that is different to the anchoring polymer segment of the copolymeric mapping moiety, wherein the coupling polymer segment couples the anchoring polymer segment to the one or more mapping groups;

wherein the coupling polymer segment comprises polymer selected from polyacrylamide, polyvinyl alcohol, polyalkylene oxide, polyoxamers, polyhydroxyethylacrylate, poly-N-isopropylacrylamide, polydimethylamino-ethylmethacrylate, polyvinyl pyrrolidone, polyacrylicacid, polymethacrylamide, poly vinyl ester, poly vinyl amide, polysulfonated divinylbenzene, poly-L-lysine, polyaspartate, poly lactic acid, polyethyleneimine, polyalkylcyanoacrylate, polymaleic anhydride, polymaleic acid and a copolymer of two or more of said polymers; and wherein the steric stabilising polymer segment comprises a polyacrylamide-co-polyalkylene oxide block copolymer that has about 8 to about 60 polymerised acrylamide units and about 2 to about 10 polymerised alkylene oxide units.

2. The magnetic nanoparticulate material according to claim 1 having bound to its surface:

(c) copolymeric luminescent moiety comprising (i) an anchoring polymer segment having one or more binding groups that bind the polymeric luminescent moiety to the magnetic nanoparticulate material, (ii) one or more luminescent groups for emitting light or an acoustic signal in response to light that enables in vivo location visualisation of the magnetic nanoparticulate material, and (iii) a coupling polymer segment that is different to the anchoring polymer segment of the copolymeric luminescent moiety, wherein the coupling polymer segment couples the anchoring polymer segment to the one or more luminescent groups; and wherein the coupling polymer segment comprises polymer selected from polyacrylamide, polyvinyl alcohol, polyalkylene oxide, polyoxamers, polyhydroxyethylacrylate, poly-N-isopropylacrylamide, polydimethylamino-ethylmethacrylate, polyvinyl pyrrolidone, polyacrylicacid, polymethacrylamide, poly vinyl ester, poly vinyl amide, polysulfonated divinylbenzene, poly-L-lysine, polyaspartate, poly lactic acid, polyethyleneimine, polyalkylcyanoacrylate, polymaleic anhydride, polymaleic acid and a copolymer of two or more of said polymers.

3. The magnetic nanoparticulate material according to claim 2, wherein the one or more luminescent groups are selected from indocyanine green, sulfo-Cy3, sulfo-Cy5, and sulfo-Cy7.

4. The magnetic nanoparticulate material according to claim 1, wherein the coupling polymer segment consists of polyacrylamide.

5. The magnetic nanoparticulate material according to claim 1, wherein the steric stabilising polymer segment has from 10 to 70 polymerised monomer residue units.

6. The magnetic nanoparticulate material according to claim 1, wherein the coupling polymer segment has from 15 to 100 polymerised monomer residue units.

7. The magnetic nanoparticulate material according to claim 1, wherein the coupling polymer segment has more polymerised monomer residue units than the steric stabilising polymer segment.

8. The nanoparticulate material according to claim 1, wherein the magnetic nanoparticulate material comprises iron (Fe), maghemite ($\gamma$-$Fe_2O_3$), magnetite ($Fe_3O_4$) or a combination thereof.

9. The magnetic nanoparticulate material according to claim 1, wherein the agent that specifically binds to fibroblast activation protein (FAP) is selected from a small molecule inhibitor and an antibody, or antigen-binding fragment thereof.

10. A composition suitable for administration to a subject, the composition comprising the magnetic nanoparticulate material according to claim 1 in a pharmacologically acceptable liquid carrier.

11. A method for mapping a tumour margin in a subject, the method comprising:

a. administering the magnetic nanoparticulate material according to claim 1 or composition according to claim 10 to the subject; and b. detecting the magnetic nanoparticulate material, wherein the magnetic nanoparticulate material accumulates in the tumour microenvironment, thereby mapping the tumour margin.

12. A method for diagnosing cancer, the method comprising:

a. administering the magnetic nanoparticulate material according to claim 1 or composition according to claim 10 to a subject; and b. detecting the magnetic nanoparticulate material;

wherein the detection of accumulated magnetic nanoparticulate material in tissue of the subject indicates that the subject has cancer.

13. A method for treatment of cancer in a subject in need thereof, the method comprising:

a. administering the magnetic nanoparticulate material according to claim 1 or composition according to claim 10 to the subject;

b. detecting a site in the subject where the magnetic nanoparticulate material accumulates; and c. administering an effective amount of a treatment for said cancer at the site of magnetic nanoparticulate material detection in step (b).

* * * * *